(12) United States Patent
Cindrich et al.

(10) Patent No.: US 7,507,222 B2
(45) Date of Patent: Mar. 24, 2009

(54) METHOD AND APPARATUS FOR SHIELDING THE TIP OF A CATHETER INTRODUCER NEEDLE

(75) Inventors: Christopher N. Cindrich, Draper, UT (US); Glade H. Howell, Sandy, UT (US); Weston F. Harding, Lehi, UT (US); Joseph Frodsham, Kaysville, UT (US); Chad Adams, Cedar Hills, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 302 days.

(21) Appl. No.: 10/477,348
(22) PCT Filed: Jun. 20, 2003
(86) PCT No.: PCT/US03/19666
§ 371 (c)(1), (2), (4) Date: Nov. 7, 2003
(87) PCT Pub. No.: WO2004/007013
PCT Pub. Date: Jan. 22, 2004

(65) Prior Publication Data
US 2005/0080378 A1  Apr. 14, 2005

Related U.S. Application Data

(63) Continuation-in-part of application No. 10/320,960, filed on Dec. 17, 2002, now Pat. No. 6,652,490, which is a continuation of application No. 09/499,331, filed on Feb. 4, 2000, now abandoned, which is a continuation-in-part of application No. 09/312,335, filed on May 14, 1999, now Pat. No. 6,379,333, which is a continuation-in-part of application No. 09/057,718, filed on Apr. 9, 1998, now Pat. No. 6,004,294, which is a continuation-in-part of application No. 09/717,148, filed on Nov. 21, 2000, which is a continuation-in-part of application No. 09/590,600, filed on Jun. 9, 2000, now abandoned, which is a continuation-in-part of application No. 09/312,335, filed on May 14, 1999, now Pat. No. 6,379,333, which is a continuation-in-part of application No. 09/057,718, filed on Apr. 9, 1998, now Pat. No. 6,004,294.

(60) Provisional application No. 60/390,499, filed on Jun. 20, 2002.

(51) Int. Cl.
A61M 5/00 (2006.01)
A61M 5/32 (2006.01)
(52) U.S. Cl. .................. 604/198; 604/110; 604/164.08
(58) Field of Classification Search ............ 604/164.01, 604/164.08, 192, 198, 110, 263
See application file for complete search history.

(56) References Cited

U.S. PATENT DOCUMENTS 4,755,170 A  7/1988  Golden ........................ 604/52
(Continued)

FOREIGN PATENT DOCUMENTS

EP  0 750 916 A2  1/1997
(Continued)

*Primary Examiner*—Kevin C Sirmons
*Assistant Examiner*—Andrew M Gilbert
(74) *Attorney, Agent, or Firm*—Mony R. Ghose; Craig Metcalf; Kirton & McConkie

(57) ABSTRACT

A medical needle assembly includes a needle cannula having a body and a tip. The tip is disposed at a distal end of the cannula. An elongate member has a first end and a second end. The first end is fixedly attached to the body of the needle cannula at a connection point and the second end extends radially outward from the needle body. A shield is slidingly mounted to the needle for movement between a proximal position to a distal position. The shield includes a shield body having a central chamber, a distal end and a proximal end as well as a plate secured to the shield body and defining an aperture. As the shield is moved from the proximal position to the distal position, the place displaces the second end of the elongate member to a position near the needle cannula, permitting the elongate member to pass through the aperture. When the shield is in the distal position, the send end of the elongate member extends radially outward from the needle body, preventing passage of the elongate member through the aperture. The elongate member may be a leaf spring. A feature may be secured to the body of the cannula to restrict movement of the shield with respect to the needle.

11 Claims, 26 Drawing Sheets

U.S. PATENT DOCUMENTS

| | | | | |
|---|---|---|---|---|
| 4,799,495 | A | * | 1/1989 | Hawkins et al. ............. 600/567 |
| 4,810,248 | A | | 3/1989 | Masters et al. .............. 604/192 |
| 4,816,024 | A | | 3/1989 | Sitar et al. .................. 604/192 |
| 4,832,696 | A | | 5/1989 | Luther et al. ................ 604/164 |
| 4,834,718 | A | | 5/1989 | McDonald ................... 604/195 |
| 4,846,811 | A | | 7/1989 | Vanderhoof ................. 604/263 |
| 4,917,669 | A | | 4/1990 | Bonaldo ..................... 604/164 |
| 4,929,241 | A | | 5/1990 | Kulli ........................ 604/263 |
| 4,944,725 | A | | 7/1990 | McDonald ................... 604/164 |
| 4,964,854 | A | | 10/1990 | Luther ........................ 604/166 |
| 4,978,344 | A | | 12/1990 | Dombrowski et al. ........ 604/198 |
| 4,994,041 | A | | 2/1991 | Dombrowski et al. ........ 604/164 |
| 5,030,212 | A | * | 7/1991 | Rose .......................... 604/263 |
| 5,049,136 | A | | 9/1991 | Johnson ...................... 604/198 |
| 5,051,109 | A | | 9/1991 | Simon ........................ 604/263 |
| 5,053,017 | A | | 10/1991 | Chamuel ..................... 604/192 |
| 5,084,023 | A | * | 1/1992 | Lemieux ................ 604/167.02 |
| 5,085,648 | A | | 2/1992 | Purdy et al. .................. 604/198 |
| 5,135,504 | A | | 8/1992 | McLees ....................... 604/164 |
| 5,147,327 | A | | 9/1992 | Johnson ...................... 604/198 |
| 5,176,655 | A | | 1/1993 | McCormick et al. ........ 604/198 |
| 5,186,712 | A | | 2/1993 | Kelso et al. .................. 604/165 |
| 5,195,983 | A | | 3/1993 | Boese |
| 5,215,525 | A | | 6/1993 | Sturman ..................... 604/164 |
| 5,215,528 | A | | 6/1993 | Purdy et al. .................. 604/164 |
| RE34,416 | E | * | 10/1993 | Lemieux ................ 604/164.08 |
| 5,279,591 | A | | 1/1994 | Simon ........................ 604/263 |
| 5,300,045 | A | | 4/1994 | Plassche, Jr. ................ 604/263 |
| 5,312,359 | A | | 5/1994 | Wallace ...................... 604/164 |
| 5,314,503 | A | * | 5/1994 | Bobrove et al. ........ 604/164.01 |
| 5,322,517 | A | | 6/1994 | Sircom et al. ................ 604/198 |
| 5,328,482 | A | | 7/1994 | Sircom et al. ................ 604/164 |
| 5,395,347 | A | | 3/1995 | Blecher et al. ............... 604/198 |
| 5,409,461 | A | | 4/1995 | Steinman .................... 604/110 |
| 5,458,658 | A | | 10/1995 | Sircom ....................... 604/192 |
| 5,558,651 | A | | 9/1996 | Crawford et al. ............. 604/263 |
| 5,562,633 | A | | 10/1996 | Wozencroft .................. 604/171 |
| 5,573,510 | A | | 11/1996 | Isaacson ..................... 604/158 |
| 5,584,809 | A | | 12/1996 | Gaba .......................... 604/110 |
| 5,584,810 | A | | 12/1996 | Brimhall |
| 5,599,310 | A | | 2/1997 | Bogert ........................ 604/164 |
| 5,601,536 | A | * | 2/1997 | Crawford et al. ............. 604/263 |
| 5,611,781 | A | | 3/1997 | Sircom et al. ................ 604/164 |
| 5,613,952 | A | | 3/1997 | Pressly, Sr. et al. .......... 604/110 |
| 5,662,610 | A | | 9/1997 | Sircom ....................... 604/110 |
| 5,676,658 | A | | 10/1997 | Erskine ....................... 604/263 |
| 5,695,474 | A | | 12/1997 | Daugherty ................... 604/162 |
| 5,697,907 | A | | 12/1997 | Gaba .......................... 604/110 |
| 5,704,919 | A | | 1/1998 | Kraus et al. .................. 604/192 |
| 5,713,876 | A | | 2/1998 | Bogert et al. ................ 604/243 |
| 5,718,688 | A | | 2/1998 | Wozencroft .................. 604/164 |
| 5,833,670 | A | | 11/1998 | Dillon et al. ................. 604/263 |
| 5,853,393 | A | | 12/1998 | Bogert ........................ 604/165 |
| 5,865,806 | A | | 2/1999 | Howell ....................... 604/164 |
| 5,879,337 | A | | 3/1999 | Kuracina et al. ............. 604/192 |
| 5,882,337 | A | | 3/1999 | Bogert et al. ................ 604/110 |
| 5,911,705 | A | | 6/1999 | Howell ....................... 604/110 |
| 5,935,109 | A | | 8/1999 | Donnan ...................... 604/164 |
| 5,951,515 | A | | 9/1999 | Osterlind .................... 604/110 |
| 6,001,080 | A | | 12/1999 | Kuracina et al. ............. 604/171 |
| 6,012,213 | A | | 1/2000 | Chang et al. ................. 29/447 |
| 6,117,108 | A | | 9/2000 | Woehr et al. |
| 6,132,401 | A | * | 10/2000 | Van Der Meyden et al. . 604/195 |
| 6,287,278 | B1 | * | 9/2001 | Woehr et al. ................ 604/110 |
| 6,786,875 | B2 | * | 9/2004 | Barker et al. ................ 600/585 |
| 2007/0112305 | A1 | * | 5/2007 | Brimhall ................ 604/164.08 |
| 2007/0250021 | A1 | * | 10/2007 | Brimhall et al. ............. 604/264 |

FOREIGN PATENT DOCUMENTS

| | | | |
|---|---|---|---|
| EP | 0 747 083 | A3 | 4/1997 |
| EP | 0 747 085 | A3 | 4/1997 |
| EP | 1 344 544 | A1 | 9/2003 |
| GB | 2 343 118 | A | 5/2000 |
| WO | WO 98/19725 | | 5/1998 |
| WO | WO 99/08742 | | 2/1999 |
| WO | WO 01/10488 | A1 | 2/2001 |
| WO | WO 01/93940 | A2 | 12/2001 |
| WO | WO 03/076526 | A2 | 10/2002 |

* cited by examiner

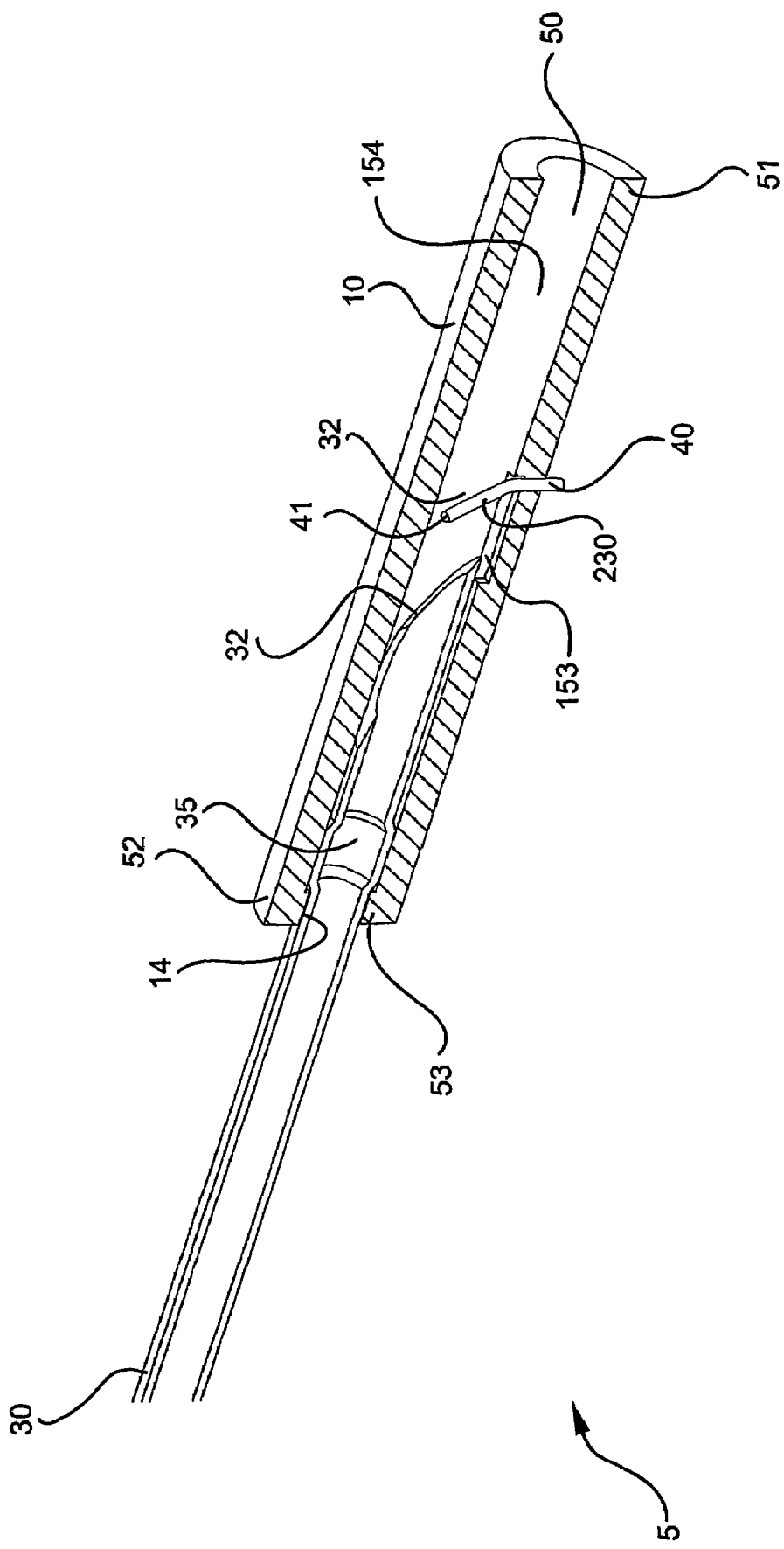

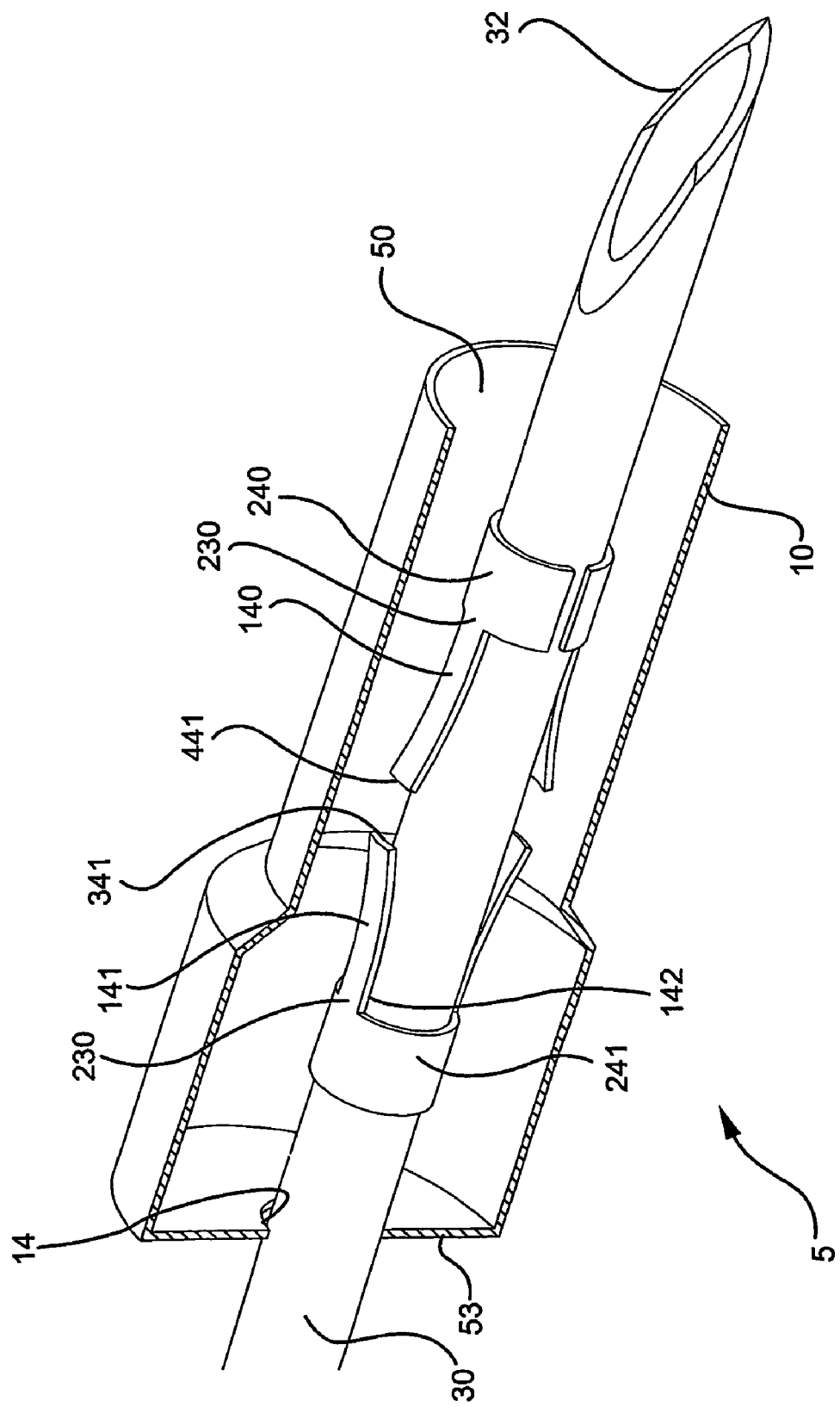

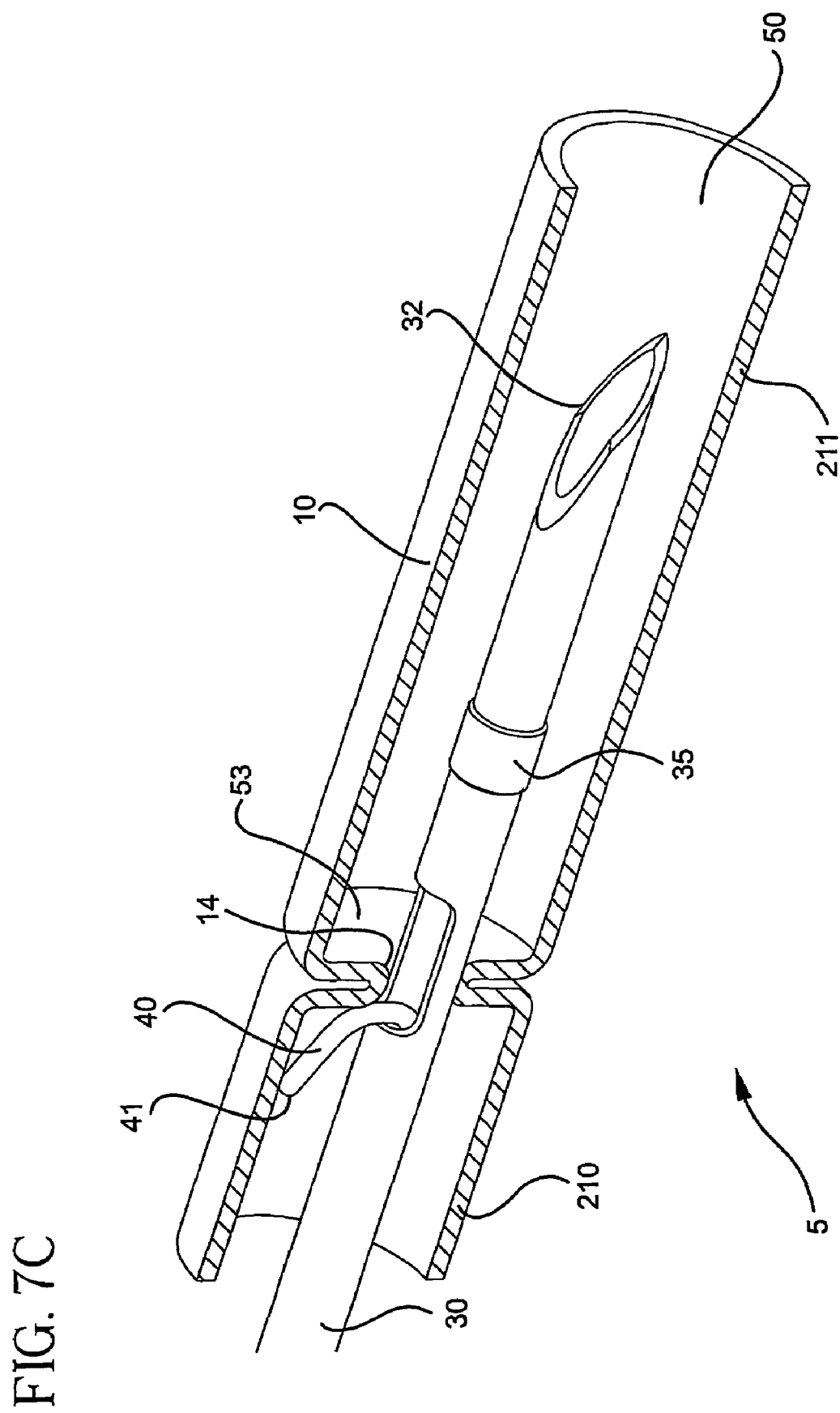

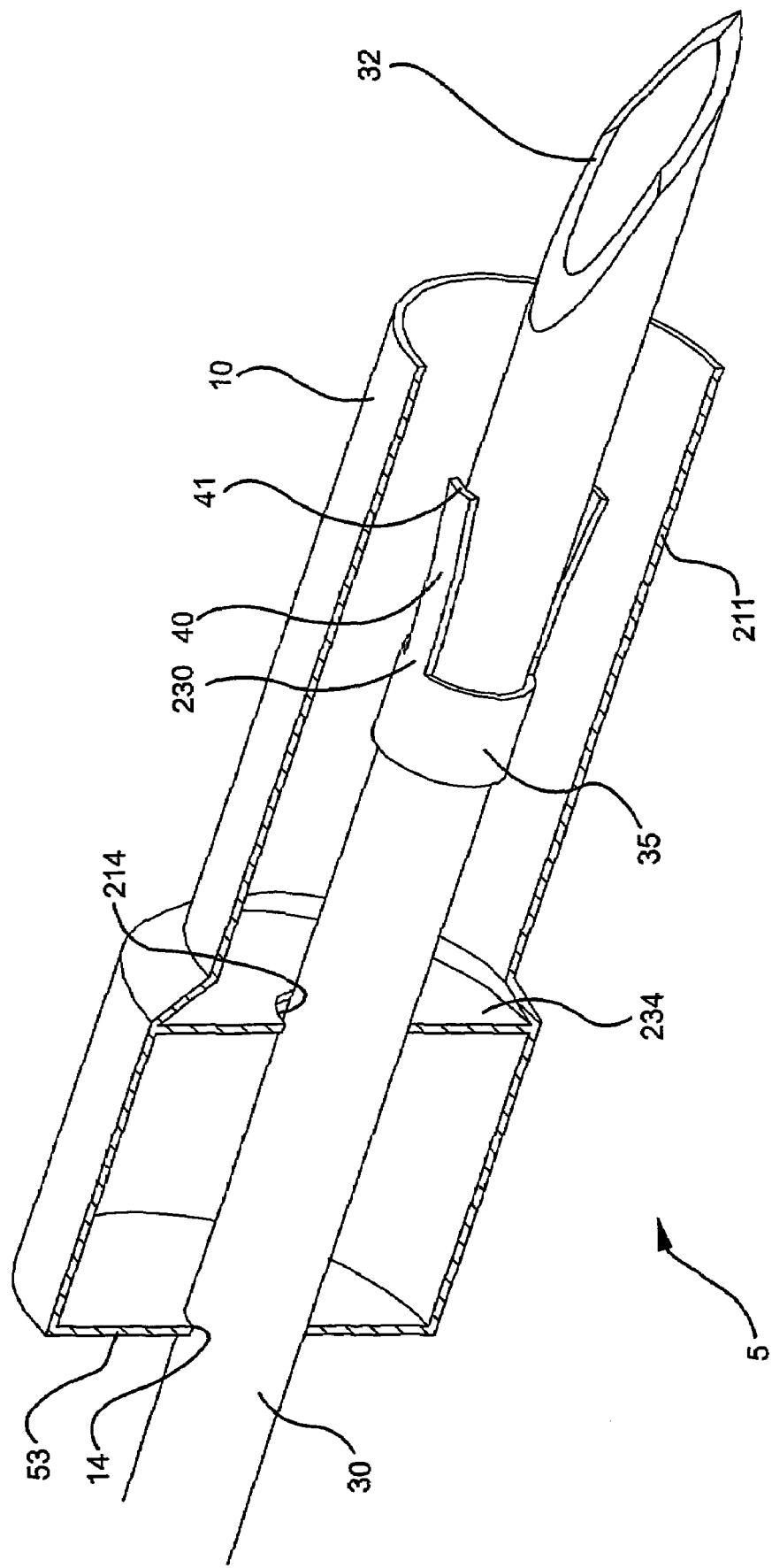

METHOD AND APPARATUS FOR SHIELDING THE TIP OF A CATHETER INTRODUCER NEEDLE

RELATED APPLICATIONS

This application claims the benefit under 35 U.S.C. 119(e) of U.S. Provisional Application Ser. No. 60/390,499 filed Jun. 20, 2002.

This application is related to the following previously filed applications, each of which is incorporated by reference: This application is a continuation-in-part of Ser. No. 10/320,960, filed Dec. 17, 2002, now U.S. Pat. No. 6,652,490 which is a continuation of Ser. No. 09/499,331, filed Feb. 4, 2000, now abandoned which is a continuation-in-part of Ser. No. 09/312,335, filed May 14, 1999, now U.S. Pat. No. 6,379,333, which is a continuation-in-part of application Ser. No. 09/057,718, filed Apr. 9, 1998, now U.S. Pat. No. 6,004,294.

This application is also a continuation-in-part of Ser. No. 09/717,148, filed Nov. 21, 2000, which is a continuation-in-part of Ser. No. 09/590,600, filed Jun. 9, 2000, now abandoned which is a continuation-in-part of Ser. No. 09/312,335, filed May 14, 1999, now U.S. Pat. No. 6,379,333, which is a continuation-in-part of application Ser. No. 09/057,718, filed Apr. 9, 1998, now U.S. Pat. No. 6,004,294.

BACKGROUND OF THE INVENTION

Field of the Invention

The subject invention relates to a needle shield assembly constructed to safely shield the sharp distal tip of a needle, and restrict distal movement of the needle tip with respect to the needle shield assembly after the tip is shielded.

Intravenous (IV) catheters are used for infusing fluid, such as normal saline solution, various medicaments and total parenteral nutrition, into a patient or withdrawing blood from a patient. Peripheral IV catheters tend to be relatively short, and are on the order of about one and one-half inches in length. A common type of IV catheter is an over-the-needle peripheral IV catheter. As its name implies, an over-the-needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly are inserted at a shallow angle through the patient's skin into a peripheral blood vessel (i.e., a smaller blood vessel that is not connected directly to the heart but is one of the branches of the central blood vessels that is directly connected to the heart). In order to verify proper placement of the assembly in the blood vessel, the clinician confirms that there is flashback of blood in the needle and in a flashback chamber located at the proximal end of the needle. Typically, the flashback chamber is formed as part of the needle hub. Once proper placement is confirmed, the clinician applies pressure to the blood vessel by pressing down on the patient's skin near the distal tip of the introducer needle and the catheter. This finger pressure occludes further blood flow through the introducer needle. The clinician withdraws the introducer needle, leaving the catheter in place, and attaches a fluid-handling device to the catheter hub. Once the introducer needle is withdrawn from the catheter, it is deemed a "blood contaminated sharp" and must be properly handled.

In recent years, there has been great concern over the contamination of clinicians with a patient's blood and a recognition that "blood contaminated sharps" must be immediately disposed. This concern has arisen, in part, to reduce the risks associated with spreading diseases that can be transmitted by the exchange of body fluids from an infected person to another person. Thus, it is desirable to avoid contact with the body fluid of an infected person. Various needle shields have been developed. Generally, such needle shields work for their intended purpose but could be improved. For example, some needle shields are bulky, difficult to use or require special features or techniques to be operative.

SUMMARY OF THE INVENTION

In accord with one aspect of the invention, a medical needle includes a needle cannula having a body and a tip. The tip is disposed at a distal end of the cannula. An elongate member is fixedly attached to the needle cannula at a connection point. The elongate member is displaceable from an unbiased condition remote from the needle cannula to a biased condition near the needle cannula.

In accord with certain implementations of this aspect of the invention, the needle cannula defines a notch and wherein the elongate member extends through the notch. The needle cannula includes an interior wall and the elongate member is attached to the interior wall. A ferrule is attached to the needle cannula and the elongate member is attached to the ferrule at the connection point. The elongate member is integrally formed with the ferrule. A second ferrule is attached to the needle cannula between the first ferrule and the tip, and a second elongate member is attached to the second ferrule and extends proximally from the second ferrule. The first ferrule and the second ferrule are integrally formed. The elongate member is integrally formed with the needle cannula. The elongate member is defined by a notch disposed in the needle cannula. The elongate member is a leaf spring or a wire. In the biased condition, the leaf spring is disposed within the notch.

In accord with another aspect of the invention, a medical needle assembly includes a needle cannula having a body and a tip. The tip is disposed at a distal end of the cannula. An elongate member has a first end and a second end. The first end is fixedly attached to the body of the needle cannula at a connection point and the second end extends radially outward from the needle body. A shield is slidingly mounted to the needle for movement between a proximal position to a distal position. The shield includes a shield body having a central chamber, a distal end and a proximal end as well as a plate secured to the shield body and defining an aperture. As the shield is moved from the proximal position to the distal position, the plate displaces the second end of the elongate member to a position near the needle cannula, permitting the elongate member to pass through the aperture.

Certain implementations of this aspect of the invention provide that, when the shield is in the distal position, the second end of the elongate member extends radially outward from the needle body, preventing passage of the elongate member through the aperture. The elongate member is a leaf spring or a wire. The aperture defines an aperture radius, the second end of the elongate member defines a member radius, and the aperture radius is less than the member radius. A feature is secured to the body of the cannula, the feature defines a feature radius, and the aperture radius is less than the feature radius. The plate is cylindrical and the aperture is cylindrical. A notch is defined by the needle body, and the elongate member is disposed adjacent to the notch. The shield has a length greater than the distance between the connection point and the tip of the needle.

In accord with another aspect of the invention, a medical needle assembly includes a needle cannula having a body and a tip. The tip is disposed at a distal end of the cannula. A feature is secured to the body of the cannula. A shield slidingly mounted to the needle for movement between a proximal position to a distal position. The shield includes a shield body having a central chamber, a distal end and a proximal end as well as a plate secured to the proximal end of the shield body and defining an aperture. When the shield is in the proximal position, the needle is disposed, at least in part, in the central chamber, and the needle extends through the aperture of the plate. The aperture is sized to permit passage of the needle body and to prevent passage of the feature. A flexible member has a first end, a second end and a thickness. The first end is fixedly attached to shield body and disposed within the central chamber. The second end of the flexible member is biased radially inwardly into the central chamber. When the shield is in the proximal position, the needle body biases the flexible member into a groove formed in the shield body. When the shield body is in the distal position, the flexible member is out of the groove and disposed between the needle cannula and the shield body.

Certain implementations of this aspect of the invention provide that the flexible member has a thickness such, when positioned within the central chamber out of the groove, the flexible member prevents passage of the feature. The flexible member is a wire connected to the shield at a connection point, the groove extends proximally from the connection point, and, when the shield is moved to the distal position, the wire is displaced in a distal direction.

In accord with another aspect of the invention, a medical needle assembly includes a needle cannula having a body and a tip. The tip is disposed at a distal end of the cannula. A ferrule is attached to the needle body at a point proximal to the tip. An elongate member is attached to the ferrule and has a free end extending radially outward from the cannula body. The free end defines a member radius. A shield is slidingly mounted to the needle for movement between a proximal position to a distal position. The shield includes a shield body having a central chamber, a distal end and a proximal end and a plate secured to the proximal end of the shield body, having a thickness and defining an aperture with an aperture radius. When the shield is in the proximal position, the needle is disposed, at least in part, in the central chamber, and the needle extends through the aperture of the plate. The aperture radius is smaller than the member radius.

Certain implementations of this aspect of the invention provide that a distal ferrule is attached to the body distal to the original ferrule. A distal elongate member is attached to the distal ferrule and extends in a proximal direction. The distal elongate member includes a second free end biased outwardly from the needle body to a second member radius. The aperture radius is smaller than the second member radius. The free end of the original elongate member and the distal free end are separated by a distance greater than the thickness of the plate. The proximal ferrule and the distal ferrule are integrally formed.

In accord with another aspect of the invention, a medical needle assembly includes a needle cannula having a body and a tip. The tip is disposed at a distal end of the cannula. An elongate member has a first end and a second end. The first end is fixedly attached to the body of the needle cannula at a connection point and the second end extends radially outward from the needle body. A shield is slidingly mounted to the needle for movement between a proximal position to a distal position. The shield includes a shield body having a central chamber, a distal end and a proximal end. A proximal plate is secured to the proximal end of the shield body and defines a proximal aperture. A distal plate is secured to the shield body distal to the proximal plate and defines a distal aperture. When the shield is in the proximal position, the needle is disposed, at least in part, in the central chamber, and the needle extends through the proximal aperture and the distal aperture. The distal aperture is adapted to permit passage of the elongate member in a proximal direction, and to resist passage of the elongate member in the distal direction.

Certain implementations of this aspect of the invention provide that the elongate member is integrally formed with the needle body. A feature is positioned on the needle body, and the elongate member and the feature are integrally formed. More than one elongate member is attached to the ferrule. The distal plate is pivotally attached to the shield body.

In accord with another aspect of the invention, a method of making a needle includes providing a needle cannula having a body and a tip, wherein the tip is disposed at a distal end of the cannula. An elongate member is fixedly attached to the needle cannula at a connection point. The elongate member is displaceable from an unbiased condition remote from the needle cannula to a biased condition near the needle cannula.

In accord with another aspect of the invention, a method of shielding a needle includes providing a needle cannula having a body and a tip, wherein the tip is disposed at a distal end of the cannula. An elongate member having a first end and a second end is attached to the body of the needle cannula at a connection point such that the second end extends radially outward from the needle body. A shield is slid along the needle cannula from a proximal position to a distal position such that, as the shield is moved from the proximal position to the distal position, a plate on the shield displaces the second end of the elongate member to a position near the needle cannula, thereby permitting the elongate member to pass through an aperture in the plate. Certain implementations of this aspect of the invention provide that the elongate member is displaced radially outward after passage through the aperture.

BRIEF DESCRIPTION OF THE DRAWINGS

The preferred embodiments are illustrated in the drawings in which like reference numerals refer to like elements and in which:

FIG. 5B is a perspective view shown in partial cross-section of the embodiment of FIG. 5A with the needle shield assembly moved to a distal position along the needle;

FIG. 6A is a perspective view in partial cross-section of another embodiment of the invention including elongate members extending in both the distal and proximal directions to engage a shield plate shown in an unactuated condition;

FIG. 7C is a perspective view in partial cross-section showing the embodiment of FIG. 7A in an actuated condition preventing re-emergence of the needle from the needle shield assembly;

FIG. 9A is a perspective view in partial cross-section of another embodiment of the invention including a ferrule integrally formed with elongate members in an unactuated condition;

DETAILED DESCRIPTION

As used herein, the term "proximal" refers to a location on the catheter and needle shield assembly of this invention closest to the clinician using the device and farthest from the patient in connection with whom the device is used when the device is used in its normal operation. Conversely, the term "distal" refers to a location on the catheter and needle shield assembly of this invention farthest from the clinician using the device and closest to the patient in connection with whom the device is used when the device is used in its normal operation.

Figure 1:
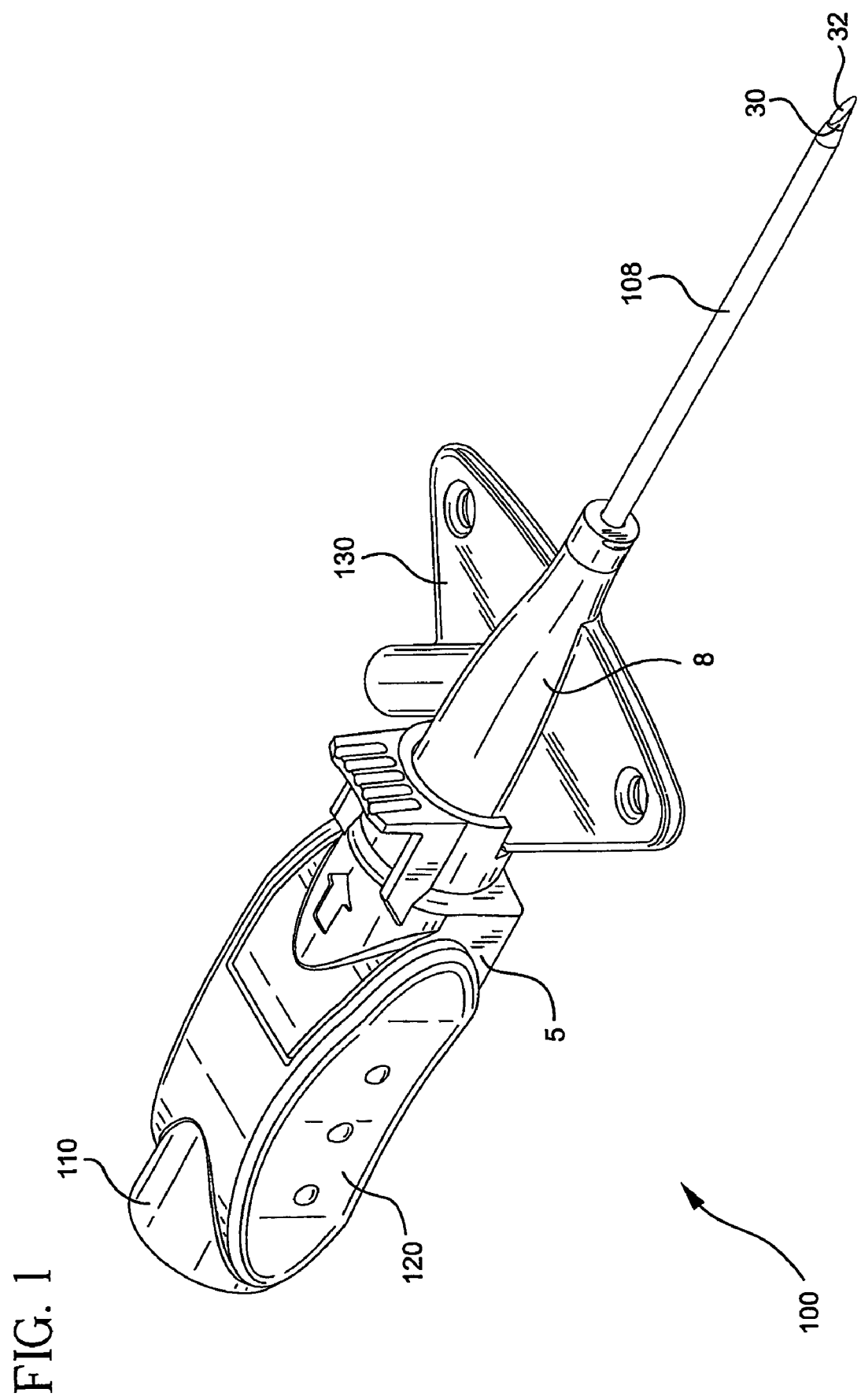
FIG. 1 is a perspective view of an over-the needle catheter assembly for use in accord with an aspect of the invention.

An introducer needle and catheter assembly 100 (also referred to as an over-the-needle catheter assembly) includes a catheter adapter 8 having a catheter 108 attached at its distal end. Wings 130 may be provided on the adapter 8. Before use and during insertion (as depicted in FIG. 1), a needle cannula 30 having a body and a tip 32, is disposed within the catheter such that the tip or distal point 32 that extends out of the distal end of the catheter. The proximal end of the needle is attached to a needle hub 110. A finger grip 120 may be incorporated into the needle hub 110. Such a structure, in conjunction with the wings 130, permits the caregiver to employ various technique for catheter Insertion, as discussed in U.S. patent application Ser. No. 09/865,915, filed May 25, 2001, incorporated herein by reference.

A shield, referred to as needle shield assembly 5, is disposed about the needle 30, preferably between the needle hub 110 and the catheter adapter 8, as shown in FIG. 1. Alternatively, the needle shield assembly 5 may be disposed completely within the catheter adapter and still practice aspects of the invention. The combination of the needle 30 and the shield 5 is referred to generally as the medical needle assembly 700 (see FIG. 2). It will be appreciated that embodiments of the invention may be implemented with either a needle shield assembly within the catheter adapter, or with a needle shield assembly disposed between the needle hub and the catheter adapter, or at other locations along the needle. Further, implementations of the invention may be employed with needles and sharps used in other devices, such as syringes and blood collection sets.

Figure 2:
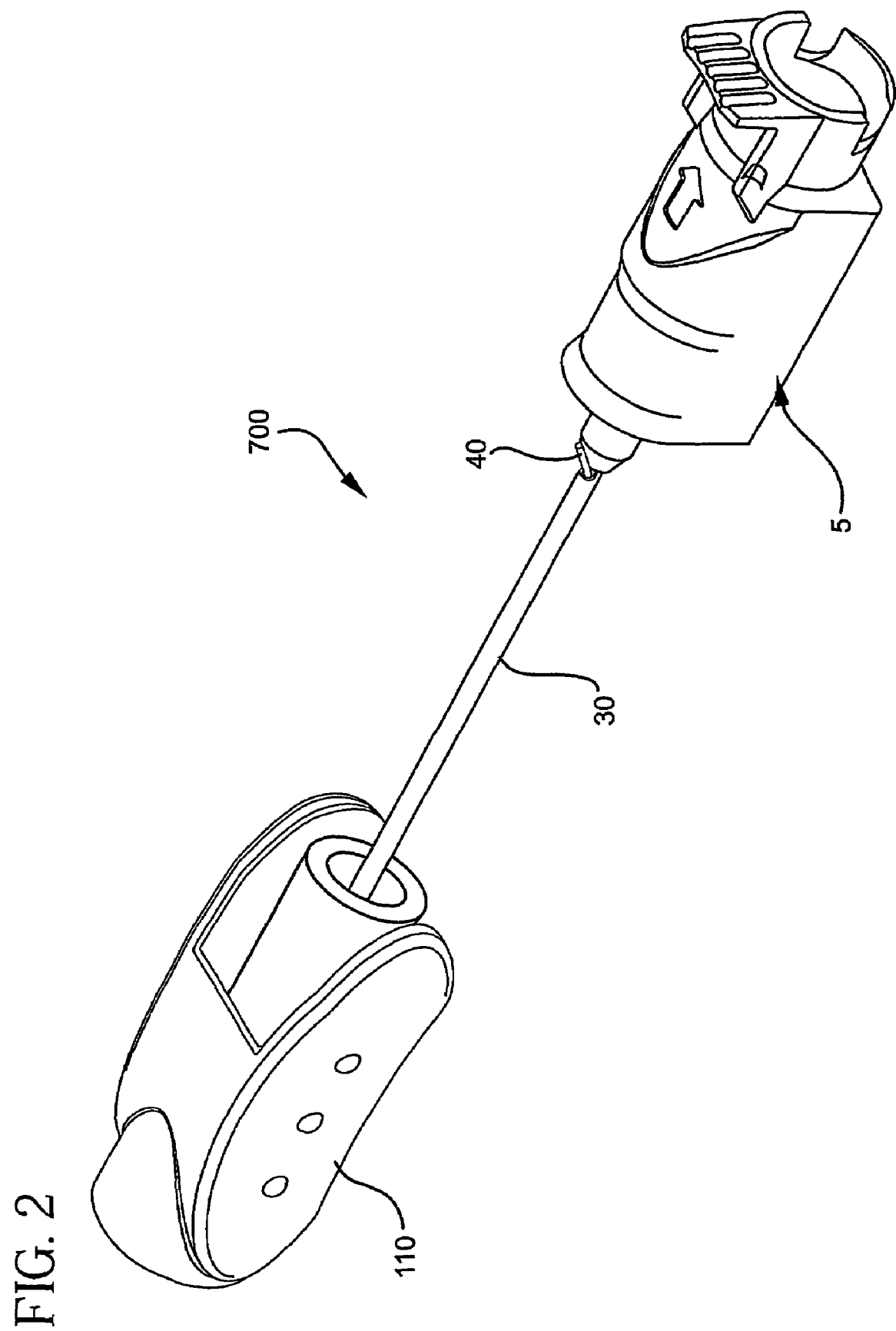
FIG. 2 is a perspective view of a medical needle assembly for use with the over-the needle catheter assembly of FIG. 1 shown in an actuated condition.

As discussed more fully below, implementations of the needle shield assembly 5 are designed such that, after insertion of the over-the-needle catheter 108 into the patient, when the needle 30 is withdrawn, the tip 32 of the needle enters the needle shield assembly. At that point, the needle shield assembly locks onto the needle tip, preventing further displacement of the shield assembly along the needle, as seen in FIG. 2. As such, the needle shield assembly cannot simply be slipped off the tip of the needle and removed. Additionally, when the needle shield assembly locks onto the needle, it prevents reemergence of the tip from the distal end of the needle shield assembly. The needle shield assembly may be designed such that it engages the catheter adapter 8 until the needle tip is withdrawn in the shield.

As depicted in FIGS. 3A-12B for the purposes of clarity, the needle shield assembly 5 may be of a simple design. It will be appreciated that finger grips, push tabs, locking flanges and hooks to engage the catheter adapter and the like may be included and still practice aspects of the invention.

The needle 30 is a cannula having a body with a distal end 130 and a proximal end 131. A sharpened tip 32 is disposed at the distal end. The needle hub 110 is secured to the proximal end 131, by gluing, welding, crimping or other manner. A notch 42 is formed in the wall of the needle 30 near the tip 32. A static feature 35 is also provided on the needle 30 at a selected distance from the tip 32. The interior wall 33 of the needle forms a chamber passing through the needle body 30. The static feature 35 is designed such that it is not capable of passage through the proximal opening 14 of shield body 10 of the needle shield assembly 5, such as disclosed in U.S. Pat. Nos. 5,558,651 and 5,215,528, both incorporated herein by reference. The static feature could be an increased diameter portion on the needle 30 (that is, an enlarged dimension, such as formed by a crimp, collar, enlarged diameter sleeve or ferrule), or a roughened surface that locks onto proximal end 12 of the needle shield assembly 5. Other structures can be employed to restrict movement of the needle tip out of the proximal end of the shield (such as a tether) and still practice aspects of the invention.

Figure 3A:
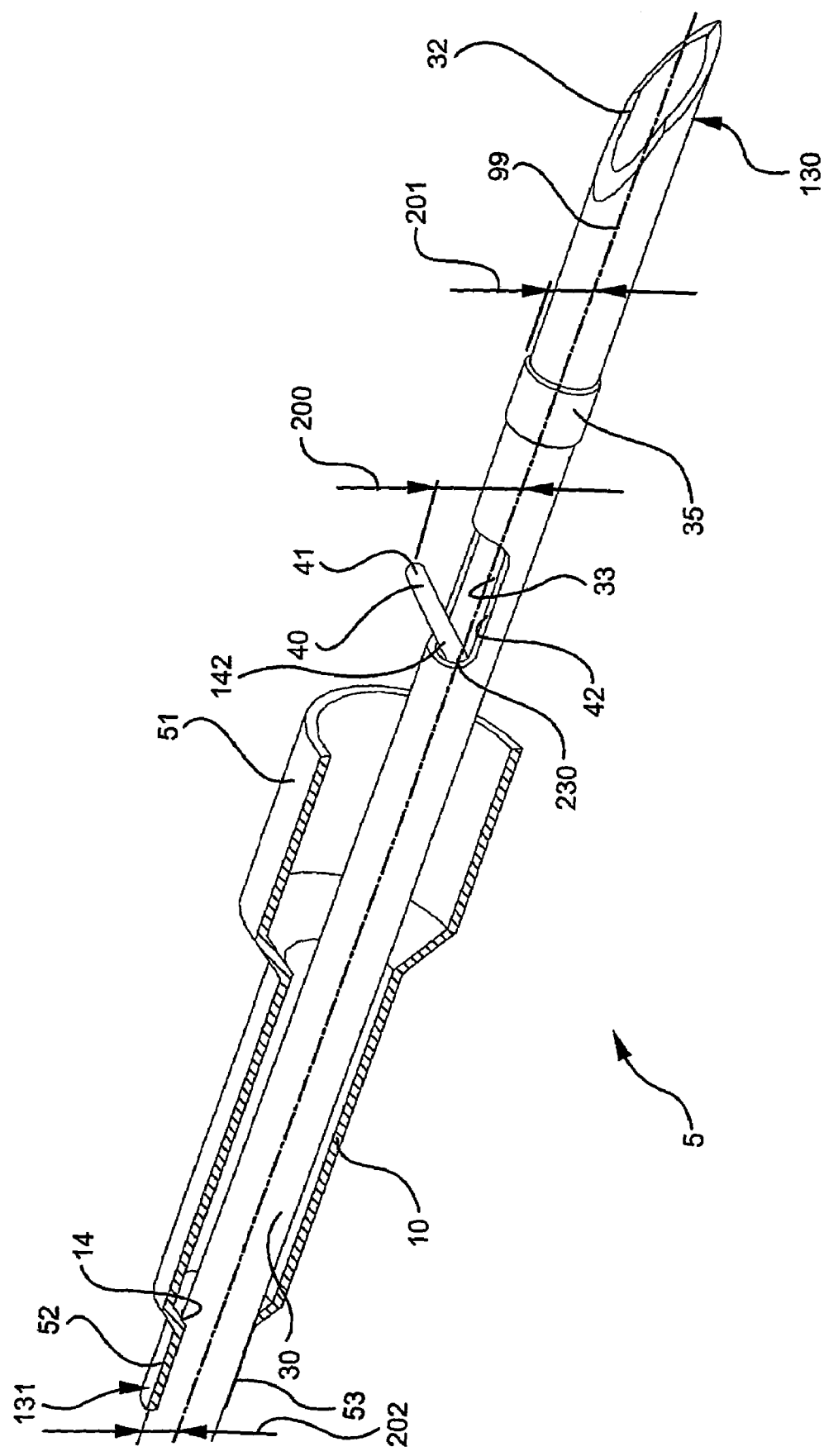
FIG. 3A is a perspective view in partial cut-away of one embodiment of the invention including a cylindrical shield plate shown in an unactuated condition.
Figure 3B:
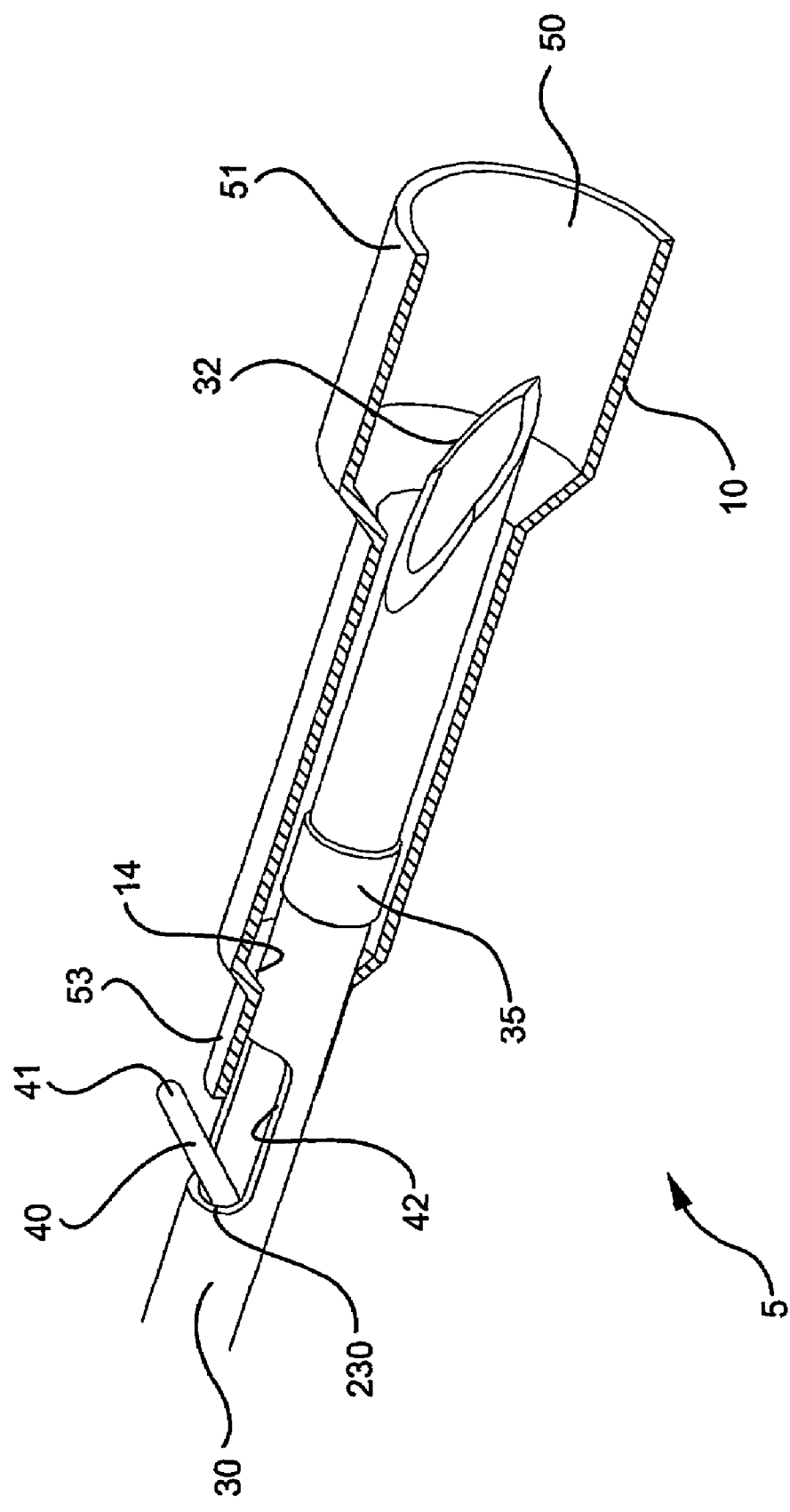
FIG. 3B is a perspective view in partial cross-section of the embodiment of FIG. 3A shown in the actuated condition.

An elongate member 40 includes at least one portion that is fixedly positioned with respect to the needle 30 and a free end 41 that can be displaced from a position remote to the needle to a position near to the needle. As depicted, the elongate member 40 is fixedly attached to the needle 30 at a connection point 230. The elongate member could be otherwise maintained in position with respect to the needle (such as fixing the elongate member to the needle hub and so forth) and still practice aspects of the invention. As shown in FIGS. 3A and 3B, the elongate member is a leaf spring formed by a flexible wire, preferably made out of steel, or other like material. It will be appreciated that other elongate members may be employed in this and other aspects of the invention. The elongate member has a first end 142, which is attached to the needle at the connection point 230, and a second or free end 41, which extends radially outward from the exterior of the needle 30. The free end 41 is preferably rounded, blunted or curved back to prevent skiving of the catheter 108 during use. As discussed below, the elongate member 40 cooperates with the needle shield assembly 5 to permit the needle shield assembly to be displaced distally toward the needle tip 32, but then prevents return of the needle shield assembly in the proximal direction. As such, the needle tip 32 remains locked within the needle shield assembly.

The elongate member 40 may be attached to the needle cannula 30 in various ways. For example, the elongate member may be crimped onto the needle cannula wall. Conversely, the needle cannula wall may be crimped onto the needle. The elongate member may be glued onto the needle cannula. The elongate member may be bent such that it snap fits onto the needle cannula (either the exterior or the interior of the cannula) and is held in place by friction The elongate member may be welded to the interior or the exterior of the needle cannula. A "keyhole" slot may be formed in the needle cannula wall. The elongate member can then be placed in the larger opening of the keyhole and then jammed into the narrow portion, such that the elongate member is retained in the pinch of the keyhole. The elongate member may also be formed by cutting out a portion of the needle wall, as discussed below. Of course, other methods may be employed to secure the wire or elongate member to the needle cannula and still practice aspects of the invention.

The shield or needle shield assembly 5 includes a shield body 10 having a central chamber 50, a distal end 51 and a proximal end 52. A plate 53 is secured to the needle shield assembly at the proximal end 52. An opening or aperture 14 is disposed in the plate. As assembled, the needle 30 is slidingly disposed in the aperture 14 such that the needle shield assembly 5 can be slidingly displaced axially along the length of the needle. Preferably, the aperture 14 is sized to prevent the passage of the static feature 35 on the needle.

As seen in FIGS. 3A and B, the plate 53 is cylindrical with a cylindrical opening 14. It will be appreciated that the plate may have various shapes and still practice aspects of the invention. For example, the plate may be conically shaped, or be a flat disc, or a series of flat discs, or any combination thereof. As will be understood, importantly, the plate will cooperate with the elongate member 40 to restrict movement of the needle shield assembly 5 with respect to the needle 30. In certain applications, the aperture 14 and plate may be configured to cooperate with the static feature 35 to prevent the needle shield assembly 5 from sliding off the tip 32 of the needle 30.

As seen in FIGS. 3A and B, the distal end 51 of the needle shield assembly 5 is open. It will be appreciated that a clip may be provided to further prevent access to the needle tip 32 after actuation. Further, the opening in the distal end 51 of the needle shield assembly 5 can be narrowed to further restrict access to the needle tip 32 when actuated. However, in the implementation depicted in FIGS. 3A and B, the opening in the distal end of the needle shield assembly should be large enough to permit the static feature 35 of the needle 30 to pass into the needle shield assembly.

In use, the needle 30 is used in its traditional manner (whether on a syringe, an introducer needle and catheter assembly, a blood sample collection set, or the like). In the case of an introducer needle and catheter assembly 100, the needle tip 32 is inserted into the patient's vein, thereby positioning the tip of the catheter 108 into the vein as well. The needle 30 is then withdrawn through the catheter, displacing the needle 30 proximally with respect to the needle shield assembly 5. As the needle shield assembly moves distally along the needle, the notch 42 and the elongate member 40 pass through the aperture 14 of the plate 53. The cylindrical wall of the plate forces the elongate member 40 radially inward into the notch 42. As such, the plate 53 may pass distally over the elongate member without substantial interference. Once the plate has passed the elongate member, the free end 41 of the elongate member then returns to its radially outward position (or "unbiased condition"). The needle shield assembly 5 continues to be displaced along the needle 30 until the static feature 35 of the needle contacts the plate 53. The aperture 14 is sized so as to prevent passage of the static feature. Consequently, the needle shield assembly 5 cannot be slipped off the tip 32 of the needle 30. Further, the free end 41 of the elongate member 40 is biased outwardly such that it extends radially beyond the outer wall of the plate 53 (specifically, beyond the aperture 14). Consequently, the needle shield assembly 5 cannot be moved back proximally along the needle 30 to re-expose the tip 32.

As shown in FIGS. 3A and B, the free end 41 of the elongate member 40 extends radially outward from the needle 30 to define a member or wire radius 200 from the axis 99. The static feature 35 also extends radially outward from the axis to define a feature radius 201. The aperture 14 in the plate 53 defines an aperture radius 202 from the axis. Preferably, the feature radius 201 is selected to be greater than the aperture radius 202 to prevent passage of the feature 35 through the aperture 14. The aperture radius 202 is selected to be less than the elongate member radius 200 to prevent passage of the elongate member 40 through the aperture as the needle 30 is moved distally with respect to the needle shield assembly 5. The elongate member 40 is angled distally and outwardly. This orientation cooperates with the cylindrical shape of the plate 53 to ensure that the free end 41 of the elongate member does not pass through the aperture 14 should the needle shield assembly be displaced proximally along the needle.

It is noted that, for the sake of clarity, the aperture radius 202, the feature radius 201 and the member or wire radius 200 are not shown in the drawings depicting other embodiments of the invention. It will be appreciated that the plate aperture 14 in the other embodiments defines an aperture radius 202, that the feature 35 (where present) in the other embodiments defines a feature radius, and that the elongate member 40 in the other embodiments define a member radius 200, as described in connection with FIG. 3A.

Figure 4A:
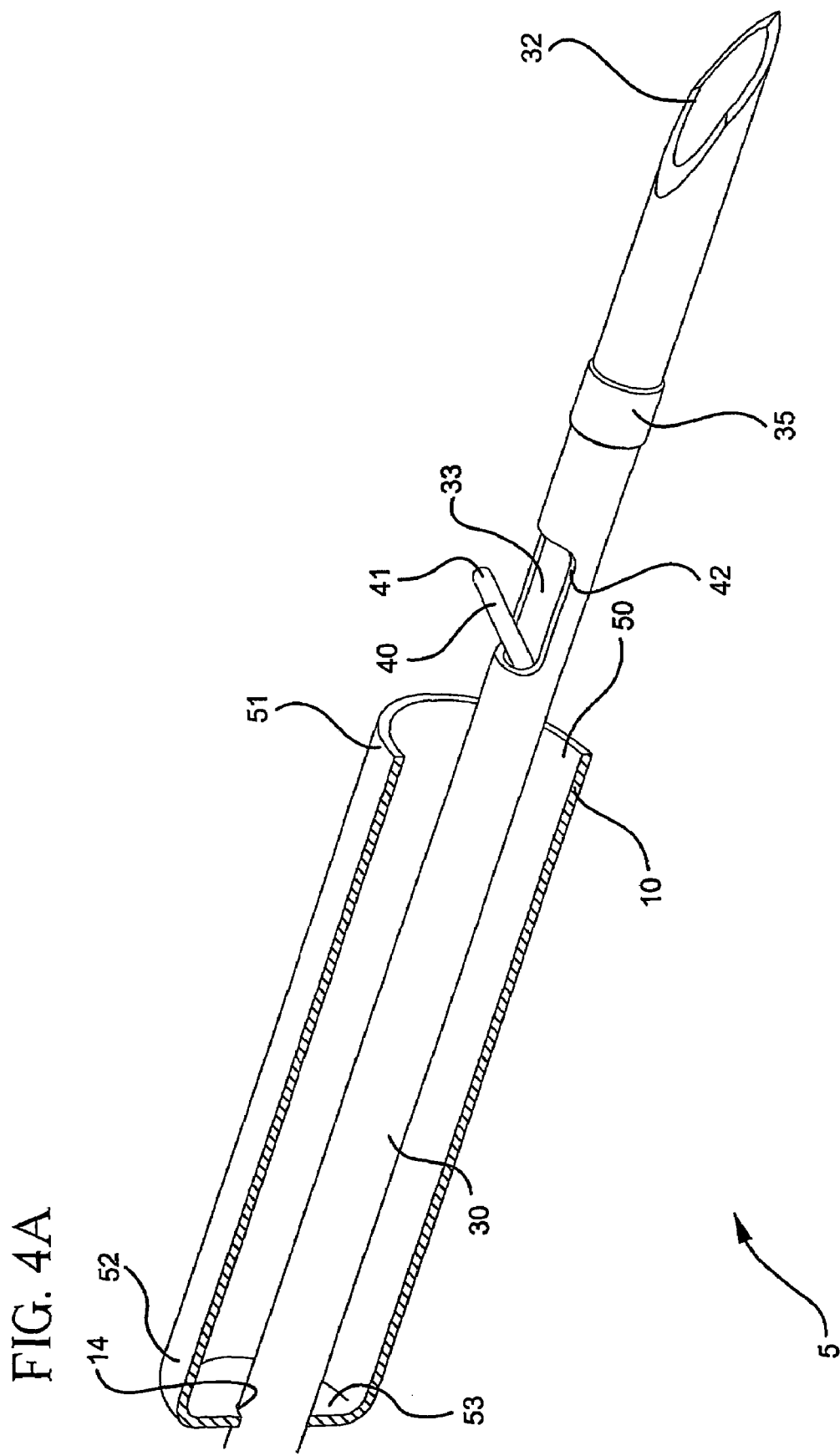
FIG. 4A is a perspective view in partial cross-section of an embodiment of the invention including a disc-shaped shield plate shown in an unactuated condition.

Referring now to the implementation of the invention depicted in FIGS. 4A and B, the plate 53 is formed in the shape of a flat disc, generally perpendicular to the axis 99 of the needle 30, while the shield body 10 extends in a cylindrical shape, distally from the disc. The aperture 14 of the disc is sized to permit passage of the elongate member 40, but to prevent passage of the static feature 35 on the needle. In implementation in which the elongate member 41 is aligned with the notch 42 (and thus capable of being deflected into the notch, out of the path of the plate 53), the aperture need only be large enough to permit passage of the needle 30.

Figure 4B:
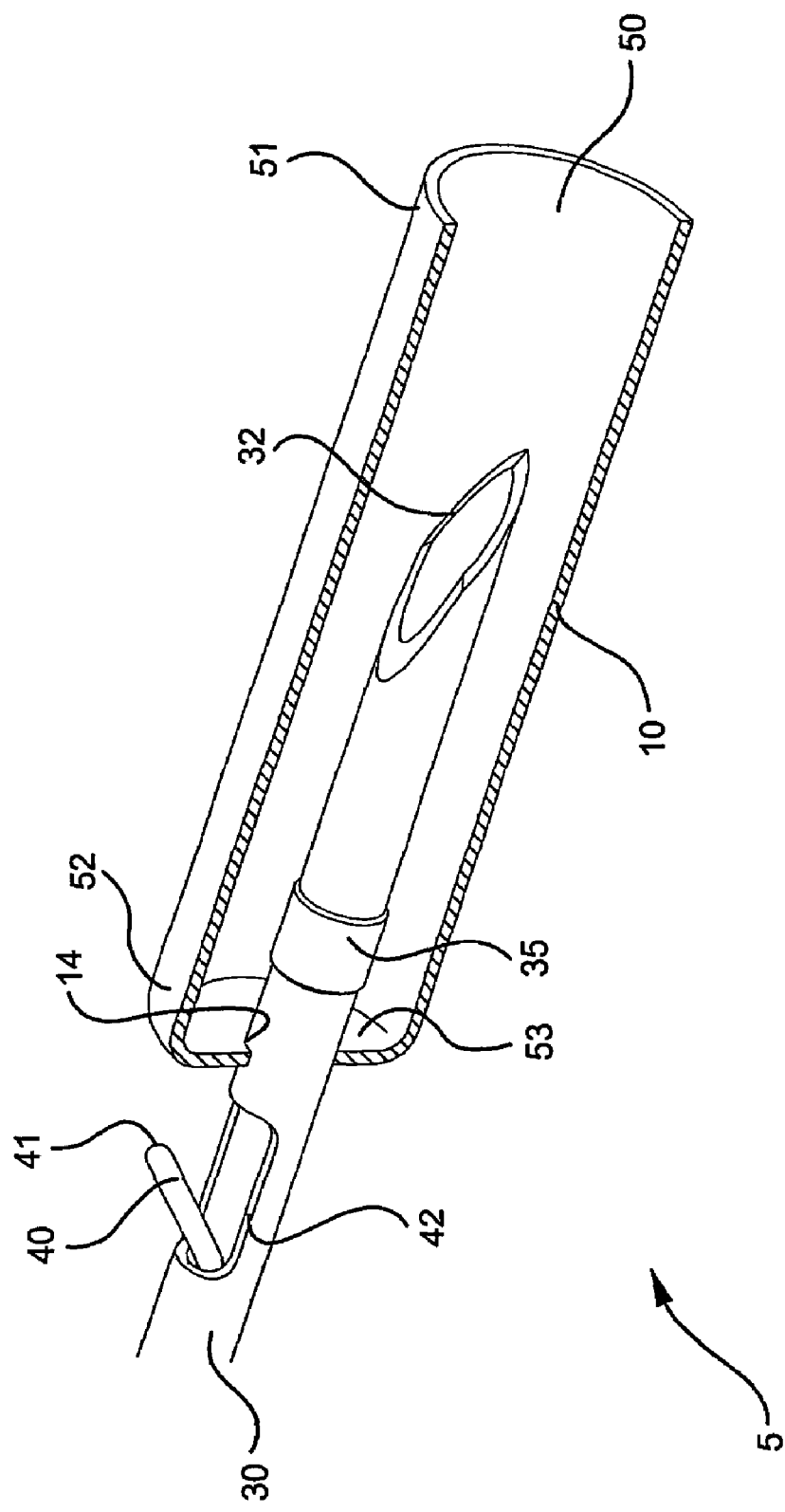
FIG. 4B is a perspective view in partial cross-section of the embodiment of FIG. 4A in an actuated condition.

In use, the needle shield assembly 5 is displaced distally along the needle 30 (compare FIG. 4A with FIG. 4B). The plate 53 rides over the elongate member 40, forcing it into the notch 47. As the plate is passed completely over the elongate member, the elongate member flexes radially outward, out of the notch, such that the free end 41 of the elongate member extends radially outward beyond the aperture 14. The needle shield assembly 5 can be moved further distally along the needle 30 until the plate 53 contacts the static feature 35. The needle shield assembly 5 cannot be moved further distally with respect to the needle 30 because of interference between the plate 53 and the static feature. The needle shield assembly 5 cannot be moved back proximally along the needle 30 because of interference between the elongate member 40 and the plate 53. Consequently, the needle shield assembly 5 can be moved only between the static feature 35 and the elongate member 40, and the tip 32 of the needle 30 is therefore trapped within the needle shield assembly 5.

Figure 5A:
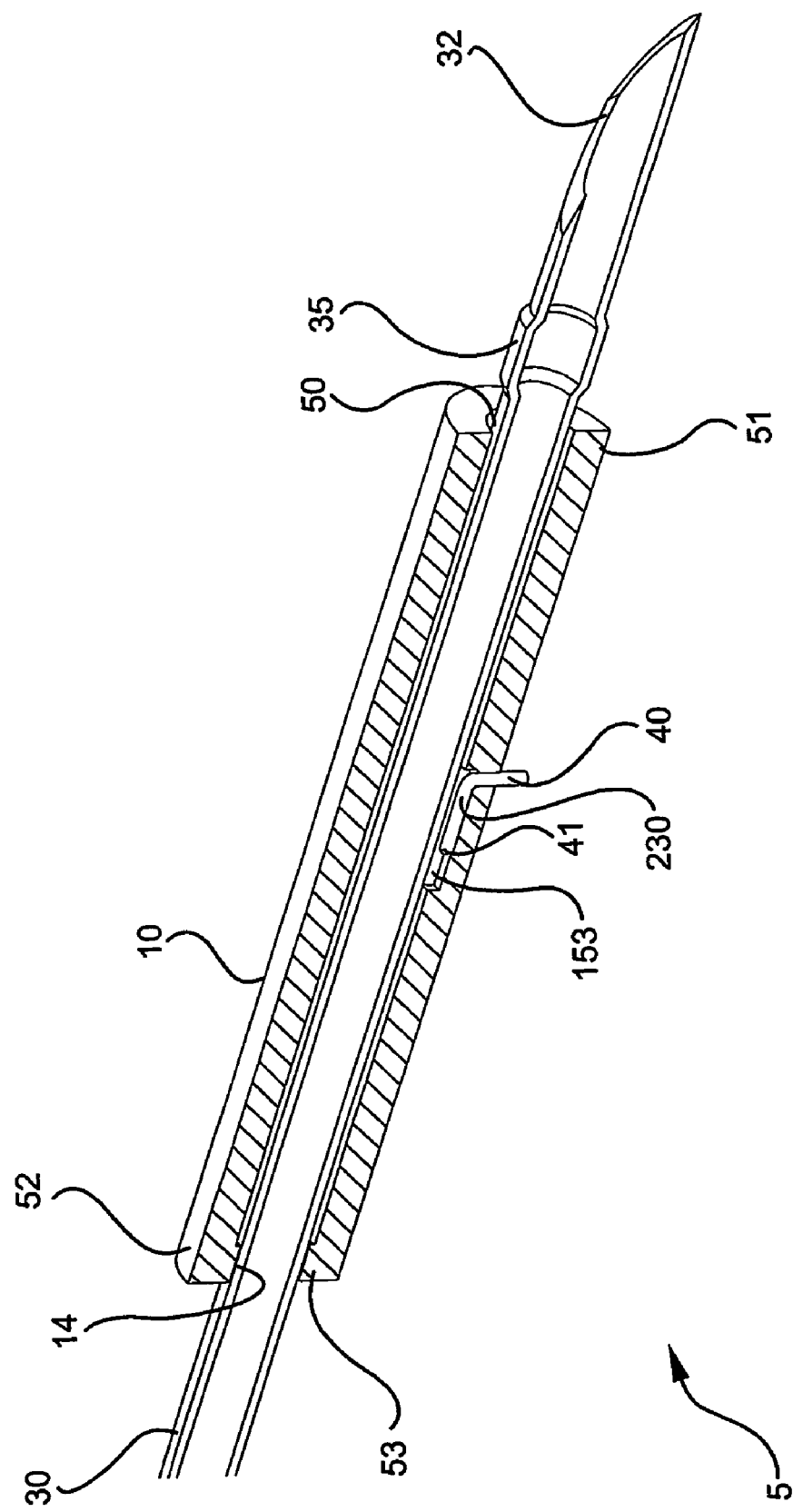
FIG. 5A is a perspective view in partial cross-section of an embodiment of the invention including an elongate member on the shield body shown in an unactuated condition.
Figure 5C:
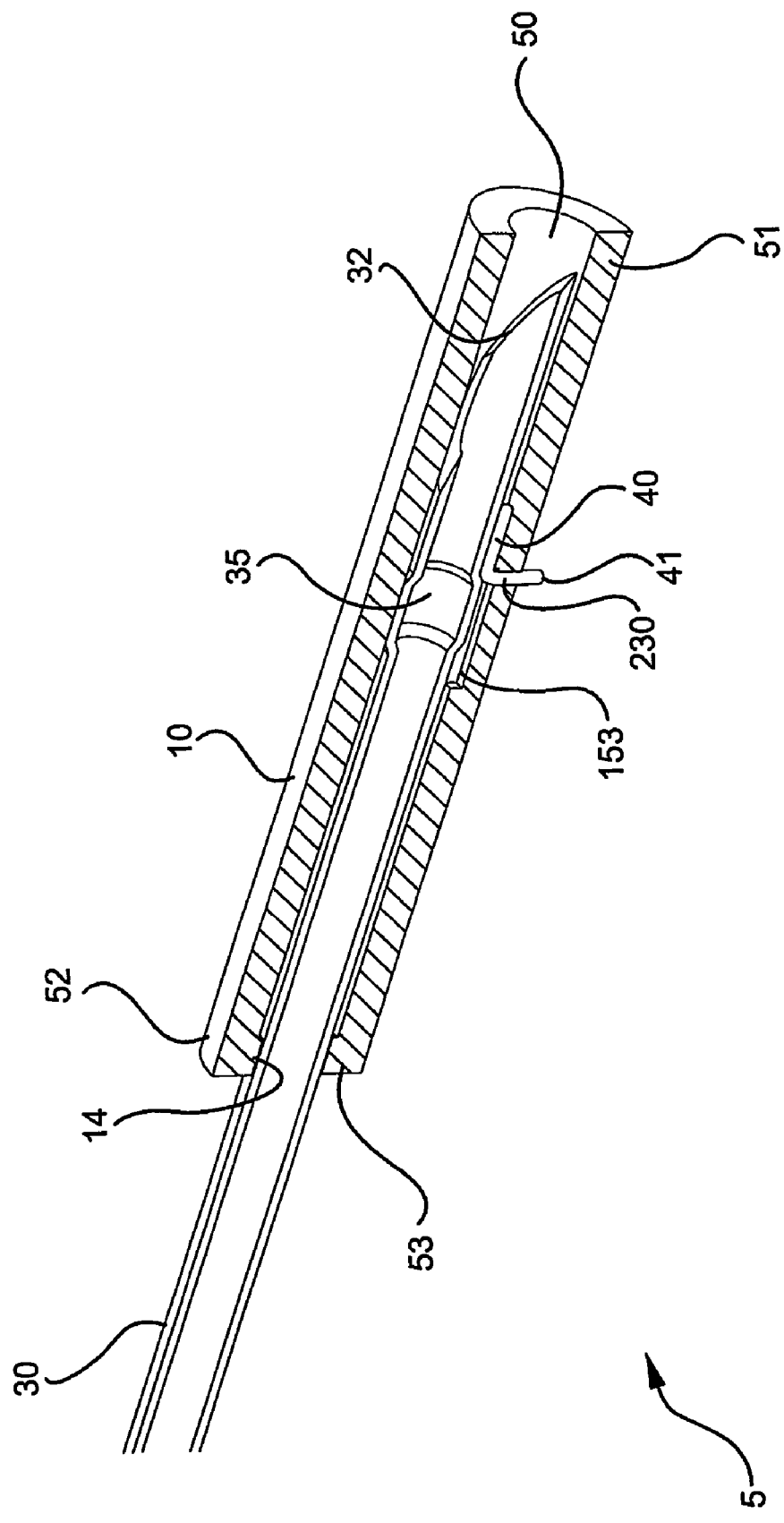
FIG. 5C is a perspective view in partial cross section showing the embodiment of FIG. 5A in an actuated condition preventing re-emergence of the needle tip from the needle shield assembly.

Referring now to FIGS. 5A-C, an implementation of the invention is depicted in which the flexible member or wire 40 is attached to the shield body 10 of the needle shield assembly 5. Specifically, the needle shield assembly 5 includes a plate 53 having an aperture 14. The aperture 14 is sized to receive the needle 30 and to permit the needle shield assembly 5 to slide along the needle in an axial direction. The shield body 10 is attached to the plate 53 and extends distally from the plate. The shield body is cylindrical, forming an internal chamber 50. The flexible elongate member, such as the wire 40, is attached to the shield body and disposed within the internal chamber 50 such that the free end 41 of the elongate member extends into the central chamber. As depicted, the elongate member extends through the wall of the shield body 10 at a connection point 230. The elongate member could be attached to the shield body in various manners and still practice aspects of the invention. For example, the elongate member could be Integrally formed with the shield body, glued to the shield body, friction fit by means of an internal collar within the shield body, welded to the shield body and so on.

As discussed above, the free end 41 of the elongate member 40 extends into the central chamber 50 of the shield body 10. The shield body is adapted to permit the elongate member to flex against its internal wall as the static feature 35 on the needle 30 passes by in the distal direction (compare FIGS. 5A and 5B). Specifically, a groove 153 is disposed in the internal wall of the shield body 10, near the connection point 230, and extending proximally therefrom. The groove is sized to receive the elongate member during actuation, as discussed below. The groove may also be an increased diameter section of the central chamber 50, extending proximally from the connection point 230.

In use, the needle shield assembly 5 is slidingly mounted onto the needle 30 such that the tip 32 of the needle is exposed for insertion. After insertion, the needle shield assembly is displaced distally along the needle. (It will be appreciated that, in the context of an over-the-needle catheter assembly 100, the needle is typically withdrawn proximally through the needle shield assembly 5.) The static feature 35 on the needle rides over the elongate member 40. Since the elongate member 40 is in the groove 153, the elongate member does not interfere with the passage of the static feature proximally through the needle shield assembly 5. The needle 30 can be withdrawn further through the needle shield assembly 5 until the static feature 35 contacts the plate 53. The aperture 14 in the plate is sized to prevent the static feature from passing therethrough. Consequently, the needle shield assembly cannot be forced off the tip 32 of the needle 30. Should the needle 30 be displaced distally with respect to the needle shield assembly, the tip 32 engages the elongate member 40, forcing it distally onto the interior wall 154 of the shield body 10. The presence of the elongate member 40 reduces the room available to permit passage of the static feature 35. Specifically, the static feature is jammed between the interior wall 154 and the elongate member 40 (see FIG. 5C), preventing the feature from moving past the connection point 230. Consequently, the needle tip is prevented from passing back out of the distal end 51 of the needle shield assembly 32.

Figure 6B:
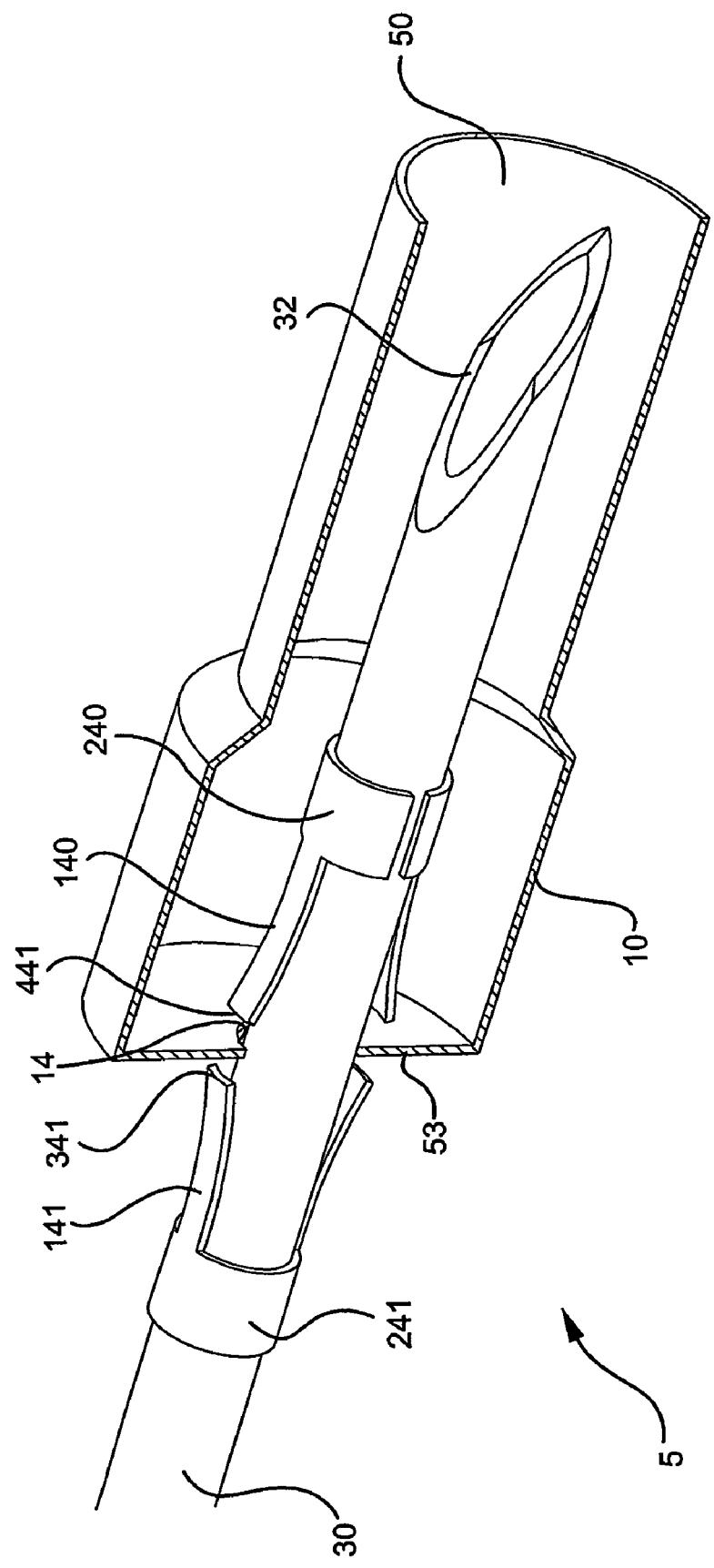
FIG. 6B Is a perspective view in partial cross-section of the embodiment of FIG. 6A shown in an actuated condition.
Figure 6C:
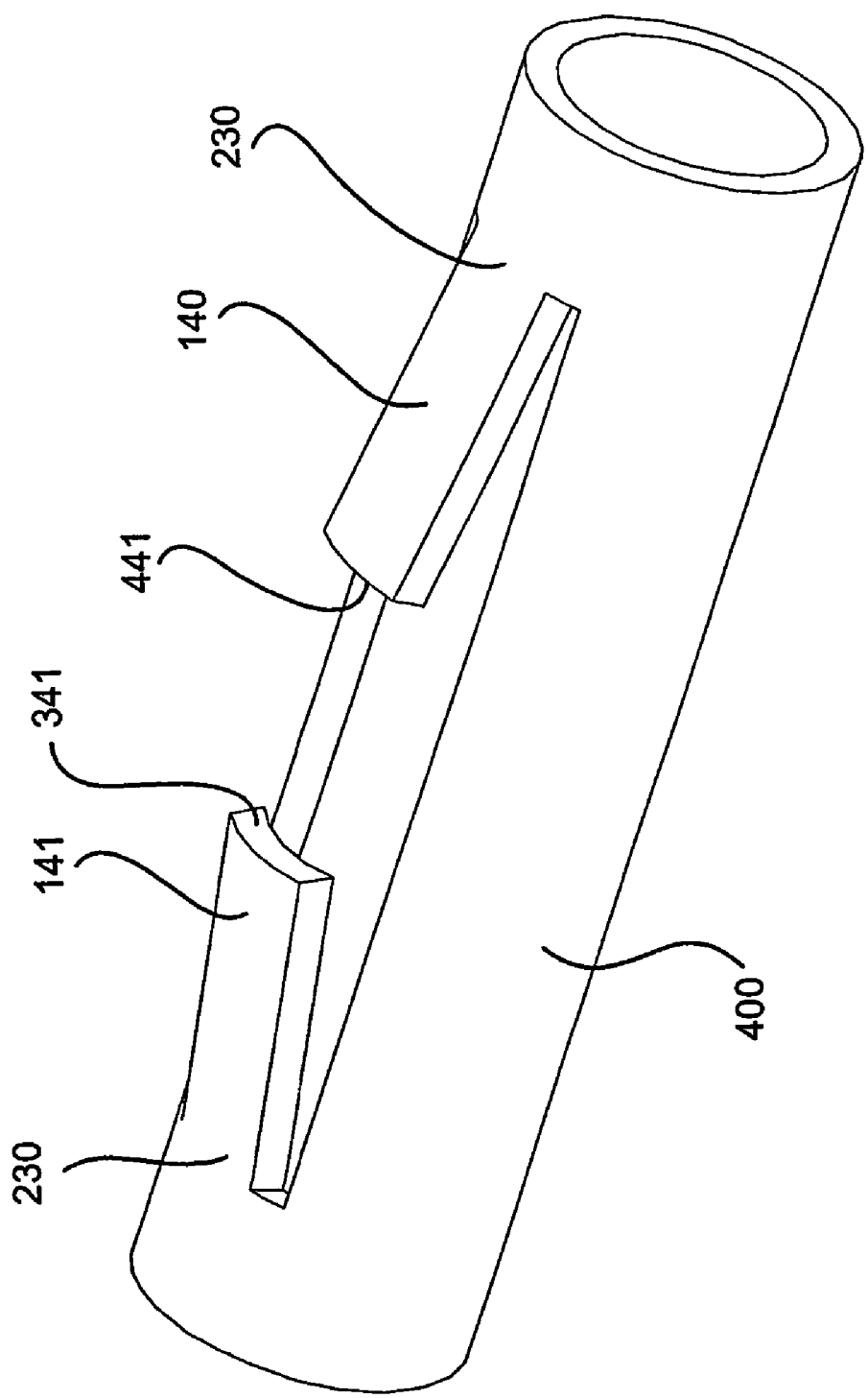
FIG. 6C is a perspective view in isolation of an integrated ferrule assembly for use in connection with the embodiment depicted in FIG. 6A.

Referring to FIGS. 6A-C, an implementation of the invention is disclosed in which the elongate members are flexible leaf springs 140, 141 mounted to the needle 30 to restrict movement of the needle shield assembly 5 in both the proximal and distal directions. A distal collar 240 is fixedly attached to the needle 30. The collar may be attached by welding, gluing, friction fitting, or other manner. Distal elongate members 140 are attached to the distal collar 240 and extend in the proximal direction. As shown, the distal elongate members 140 are integrally formed with the distal collar. The elongate members could be attached to the distal collar by gluing, welding or other manner. Further, the elongate members could be integrally formed from the needle wall (in which case, no collar would be necessary). The distal elongate members are flexible and extend radially outward from the needle 30. As depicted, the distal elongate members are leaf springs, but other flexible members, such as wires and the like, could be employed and practice aspects of the invention.

A proximal collar 241 is fixedly attached to the needle 30, and positioned proximal to the distal collar 240. As with the distal collar, the proximal collar 241 may be attached by welding, gluing, friction fitting, or other manner. Proximal elongate members 141 are attached to the proximal collar and extend in the distal direction. As shown, the proximal elongate members 141 are integrally formed with the proximal collar 241 but it is understood that the proximal elongate members could be attached to the proximal collar by gluing, welding or other manner. Further, the proximal elongate members could be integrally formed from the needle wall (in which case, no collar would be necessary). As with the distal elongate members, the proximal elongate members are flexible and extend radially outward from the needle. Again, the proximal elongate members are leaf springs, but other flexible members could be employed and practice aspects of the invention.

The free ends 341, 441 of the proximal elongate members 141 and the distal elongate members 140 approach each other but are preferably separated by a distance greater than the width of the plate 53. As shown, there is a pair each of distal elongate members 140 and proximal elongate members 141. Other numbers of elongate members could also be employed and practice aspects of the invention. While the proximal and distal collars 241, 240 are shown as distinct structures, the collars could be integrally formed into a single integrated collar 400, as shown in FIG. 6C.

In use, the needle shield assembly 5 is slidingly mounted onto the needle 30 such that the tip 32 of the needle is exposed for insertion. After insertion, the needle shield assembly 5 is displaced distally along the needle 30 until the tip 32 of the needle is within the needle shield assembly. (It will be appreciated that, in the context of an over-the-needle catheter assembly 100, the needle is typically withdrawn proximally through the needle shield assembly.) The aperture 14 of the plate 53 is sized to permit the passage of the proximal collar 241 (or the proximal portion of an integrated collar 400). The plate 53 of the needle shield assembly 5 compresses the proximal elongate members 141 against the exterior surface of the needle 30, permitting the proximal elongate members to slide through the aperture 14 of the plate. As the plate passes the free end 341 of the proximal elongate members, they spring back, moving radially outward from the needle body. In this unbiased condition, the free ends 341 of the proximal elongate members 141 extend radially beyond the aperture 14. At that point, seen in FIG. 6B, the needle shield assembly 5 cannot be moved back proximally with respect to the needle 30 because the free ends 341 of the proximal elongate members 140 would interfere with the plate 53. Similarly, further distal movement of the needle shield assembly with respect to the needle is prevented by interference between the free ends 441 of the distal elongate members 140 and the plate. Consequently, the needle shield assembly 5 cannot be moved substantially in either a proximal or distal direction with respect to the needle 30. The needle tip 32 therefore remains encased within the needle shield assembly 5.

Figure 7A:
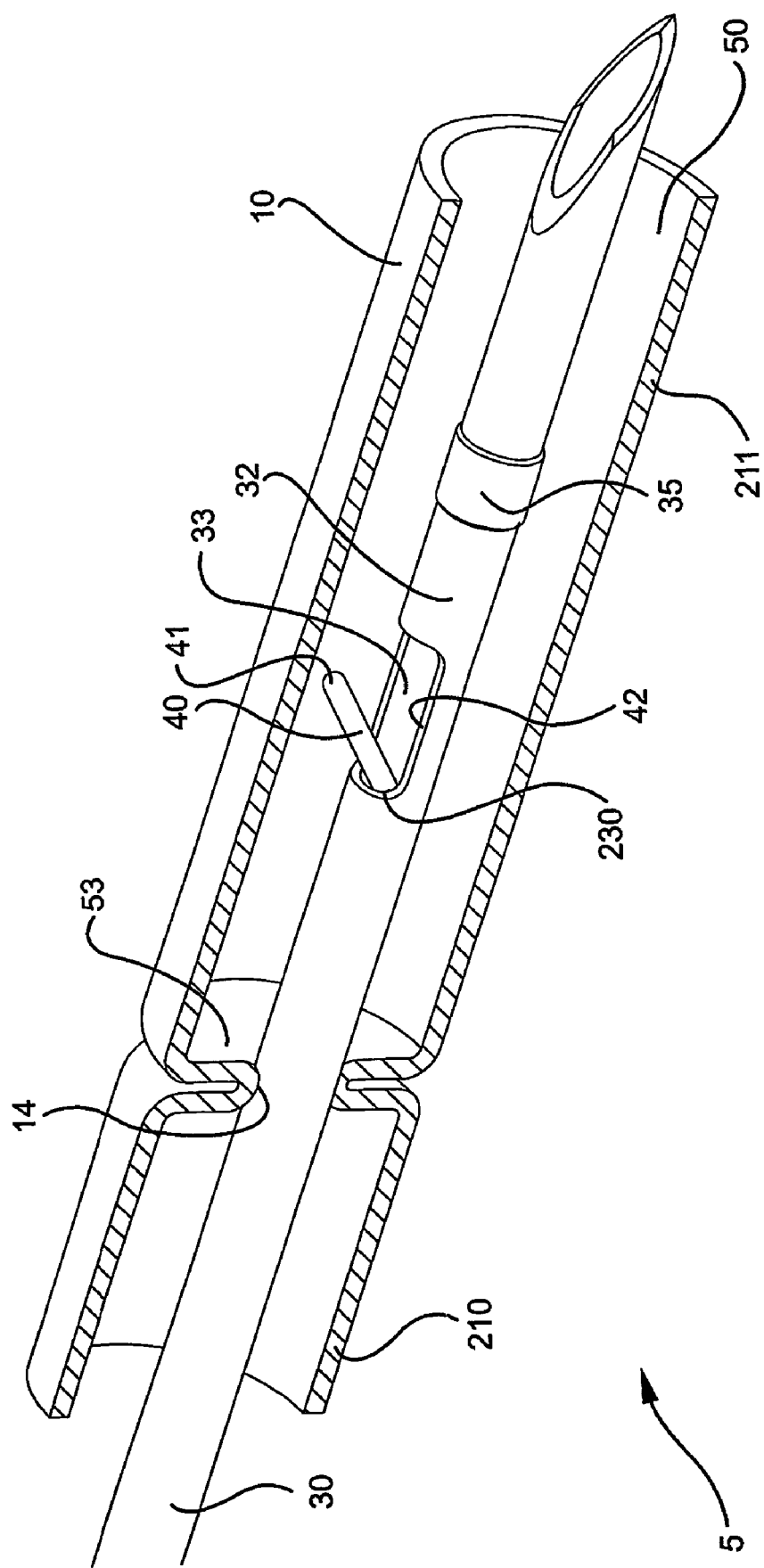
FIG. 7A is a perspective view in partial cross-section showing an embodiment of the invention including a proximal extension and an integrated shield plate in an unactuated condition.
Figure 7B:
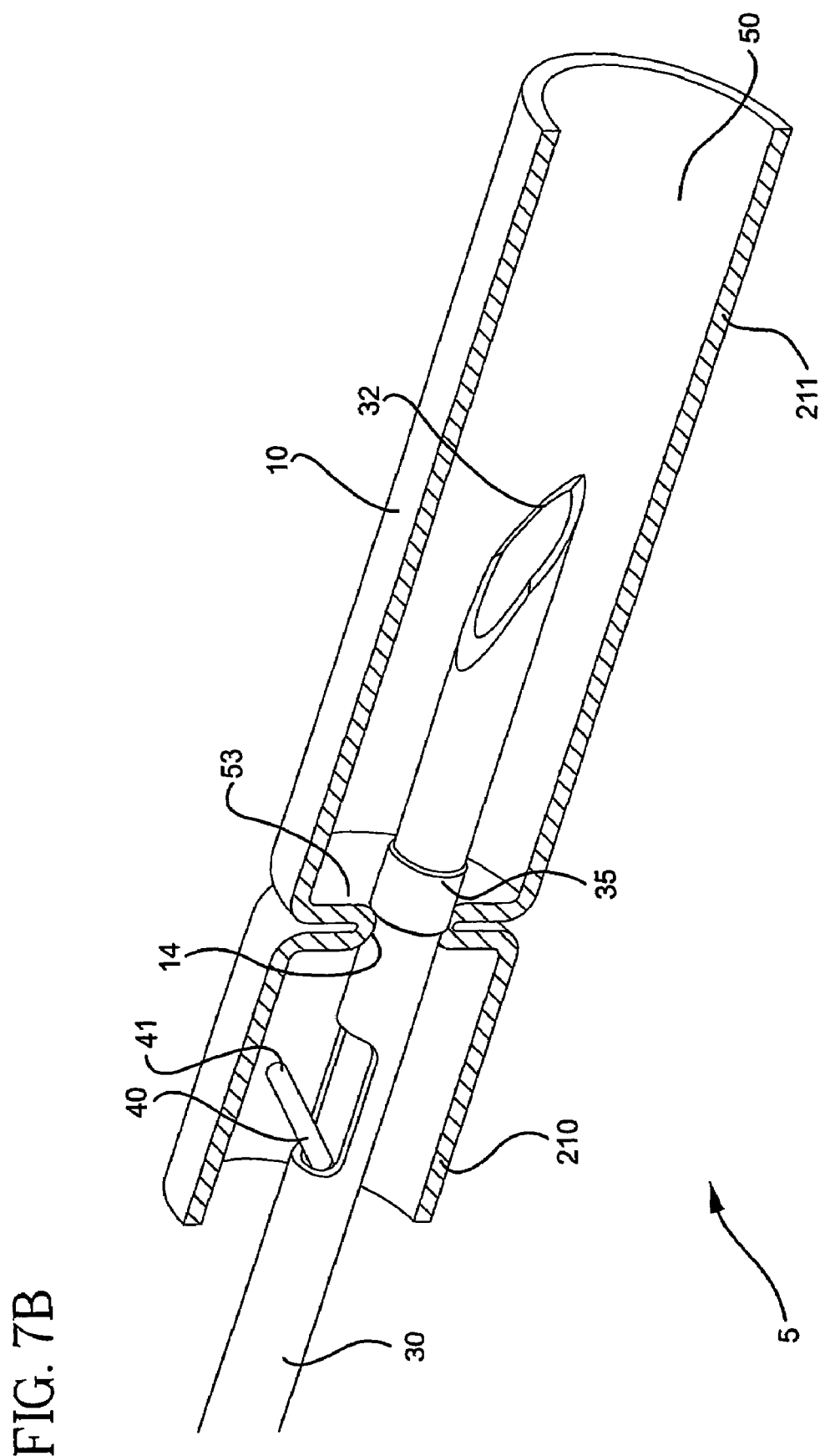
FIG. 7B is a perspective view in partial cross-section of the embodiment of FIG. 7A shown in an actuated condition.

Referring now to FIGS. 7A-C, an implementation of the invention is depicted including a proximal shield body extension 210 to limit access to the flexible elongate member 40 once locked in place in the actuated condition. Specifically, the needle shield assembly 5 includes a plate 53 having an aperture 14. A distal portion 211 of the shield body 10 is attached to the plate and extends distally therefrom. A proximal portion 210 of the shield body is attached to the plate and extends proximally therefrom. The elongate member 40 is attached to the needle 30 at a connection point 230 and extends radially outward from the needle. A static feature 35 is positioned on the needle distal to the connection point.

As depicted, the proximal portion 210 and the distal portion 211 of the shield body 10 are integrally formed with the plate 53, the plate being a narrowed or crimped portion of the shield body. The plate 53 may also have other configurations as discussed herein throughout and still practice aspects of this invention. For example, the plate could be a single disc or have an elongate cylindrical aperture. Further, the plate could be a structure separate from, but operably engaged to the shield body. The shield body itself may be formed from distinct distal portions and proximal portions that are operably connected. The static feature 35 could be replaced by distal elongate members 141, as discussed above.

In use, the needle shield assembly 5 is slidingly mounted onto the needle 30 such that the tip 32 of the needle is exposed for insertion. After insertion, the needle shield assembly 5 is displaced distally along the needle until the tip 32 of the needle is within the needle shield assembly. (It will be appreciated that, in the context of an over-the-needle catheter assembly 100, the needle is typically withdrawn proximally through the needle shield assembly.) As the plate 53 passes over the elongate member 40, the elongate member is deflected into the notch 42, permitting passage of the plate 53 distally over the elongate member. When the plate 53 has passed over the elongate member 40, the elongate member springs back out radially, into the central chamber 50 of the needle shield assembly 5 (as seen in FIG. 7B). The elongate member thus prevents the needle shield assembly 5 from moving back proximally with respect to the needle, as discussed above. The static feature 35 is sized such that it cannot pass through the aperture 14 of the plate 53. Consequently, the plate is trapped between the static feature and the elongate member, and the needle tip 32 is trapped within the needle shield assembly 5. The elongate member 40 is also encased within the proximal portion 210 of the needle shield assembly 5, reducing the ability of tampering with the elongate member's engagement of the plate 53.

Figure 8A:
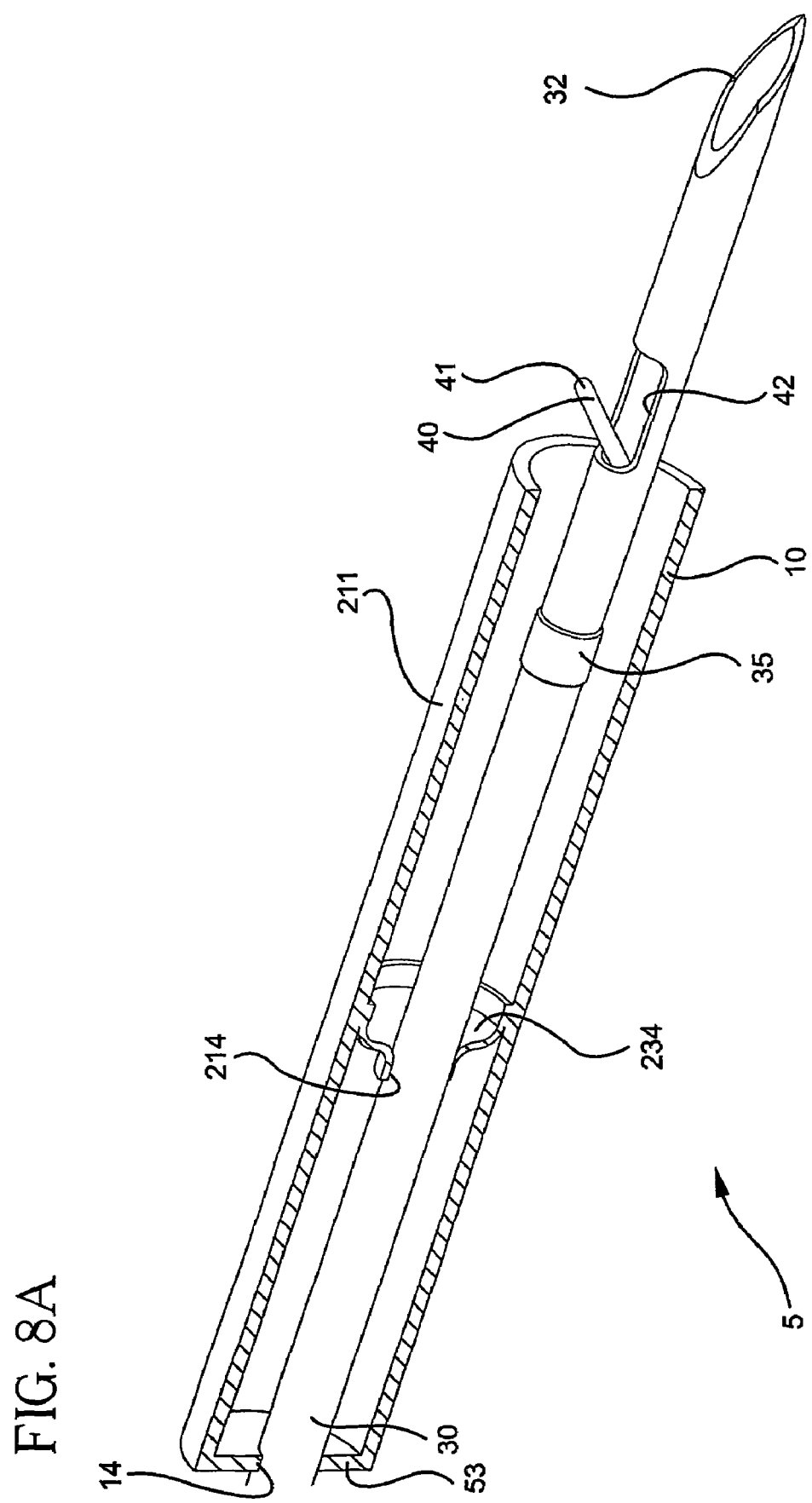
FIG. 8A is a perspective view in partial cross-section of an embodiment of the invention including a proximal plate and a distal plate shown in an unactuated condition.
Figure 8B:
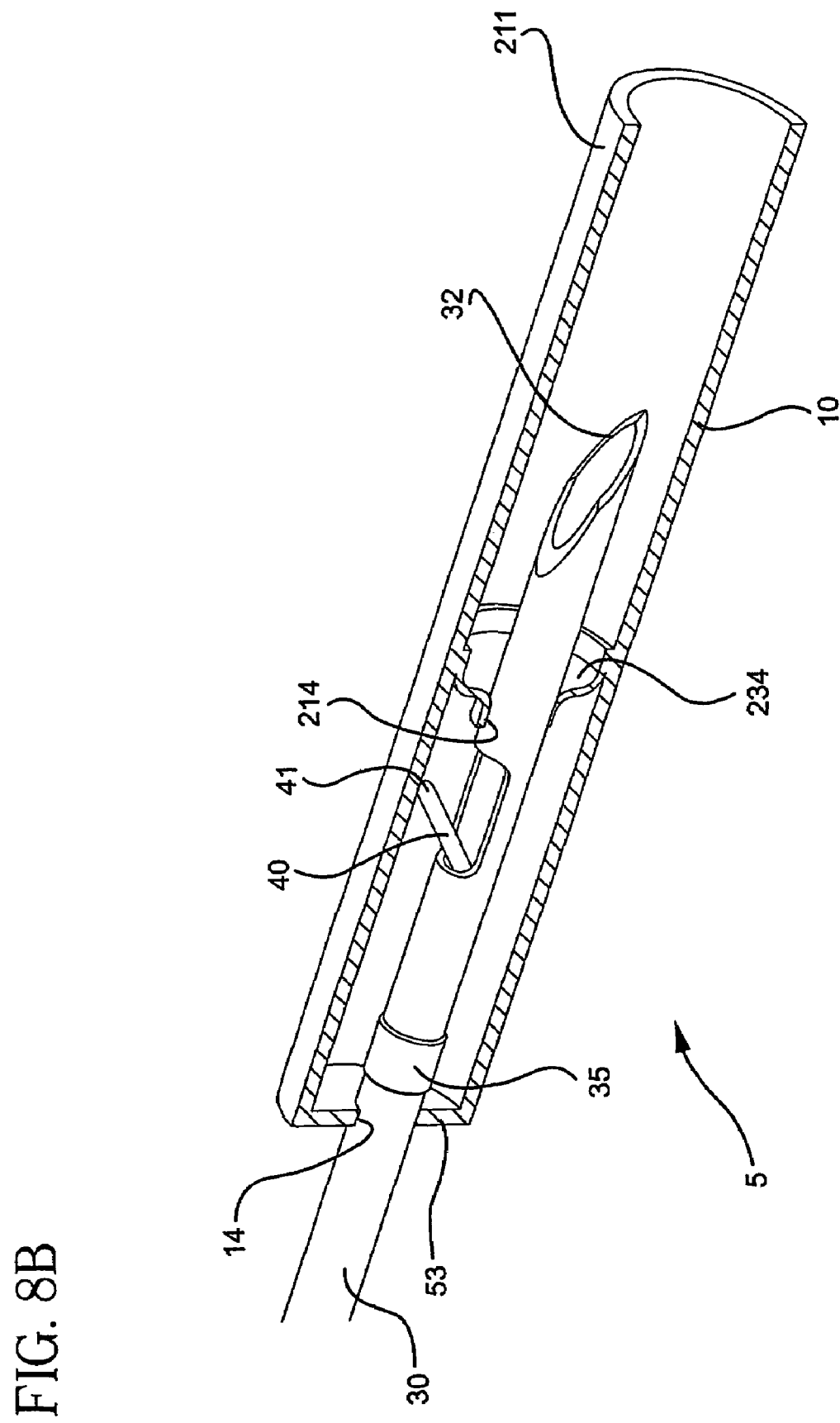
FIG. 8B is a perspective view in partial cross-section of the embodiment of FIG. 8A in an actuated condition.

Referring now to FIGS. 8A-B, an implementation of the invention is depicted in which two plates 34, 234 are employed in the needle shield assembly 5 to restrict axial movement of the needle 30 with respect to the needle shield 5. The needle shield assembly includes a proximal plate 53 having a proximal aperture 14. The shield body 10 is attached to and extends distally from the proximal plate. A distal plate 234 is attached to the shield body 10 and disposed within the central chamber 50 of the shield body. The distal plate includes a distal aperture 214. The needle 30 is disposed within the proximal aperture 14 and the distal aperture 214 such that the needle shield assembly 5 can slide axially along the needle.

The needle 30 includes a static feature 35 formed on or with the needle body. A notch 42 is disposed in the needle, positioned distal to the static feature 35. A flexible elongate member, such as a wire 40, is attached to the needle 30 at a connection point 230 near the proximal end of the notch 42. The elongate member extends out of the notch in a distal direction, and is aligned with the notch. The proximal end of the static feature and the elongate member are separated by a distance adequate to permit both structures to be positioned between the proximal plate 53 and the distal plate 234, as discussed below. A portion 211 of the shield body 10 extends beyond the distal plate 234 to ensure that the needle tip 32 is contained within the shield body 10 after actuation.

As depicted, the proximal plate 53 is a flat disc while the distal plate 234 has a funnel shape pointing in the proximal direction. It will be appreciated that the plates may have other shapes and practice aspects of the invention. For example, the plates may have cylindrical shapes or comprise expanding collars, or the like. The proximal plate 53 should include an aperture 14 sized to permit passage of the needle 30 itself, but to prevent passage of the static feature 35. Consequently, the needle shield assembly 5 may not be slipped off the tip 32 of the needle 30. The distal plate 234 is shaped and sized to permit passage of the static feature 32 and the elongate member 40 through the distal aperture 214 as the needle shield 5 is moved distally with respect to the needle, but to prevent the elongate member from passing back through the distal aperture 214 should the needle shield assembly be moved proximally along the needle.

In use, the needle shield assembly 5 is slidingly mounted onto the needle 30 such that the tip 32 of the needle is exposed for insertion. After insertion, the needle shield assembly 5 is displaced distally along the needle 30 until the tip 32 of the needle is within the needle shield assembly. (It will be appreciated that, in the context of an over-the-needle catheter assembly 100, the needle is typically withdrawn proximally through the needle shield assembly.) The static feature 35 passes through the distal aperture 214. As the needle 30 is moved further proximally, the distal plate 234 compresses the elongate member 40 into the notch 42, permitting the elongate member to pass through the distal aperture. The funnel shape of the distal plate helps direct the passage of the static feature and the compression of the elongate member. As the needle 30 is moved further proximally with respect to the needle shield assembly 5, the static feature 35 contacts the proximal plate 53, preventing further proximal movement of the needle with respect to the needle shield assembly. Should the needle 30 be urged distally with respect to the needle shield assembly 5, the elongate member 40 will engage the distal plate 234, preventing the needle tip 32 from reemerging from the distal end 211 of the needle shield assembly.

Figure 9B:
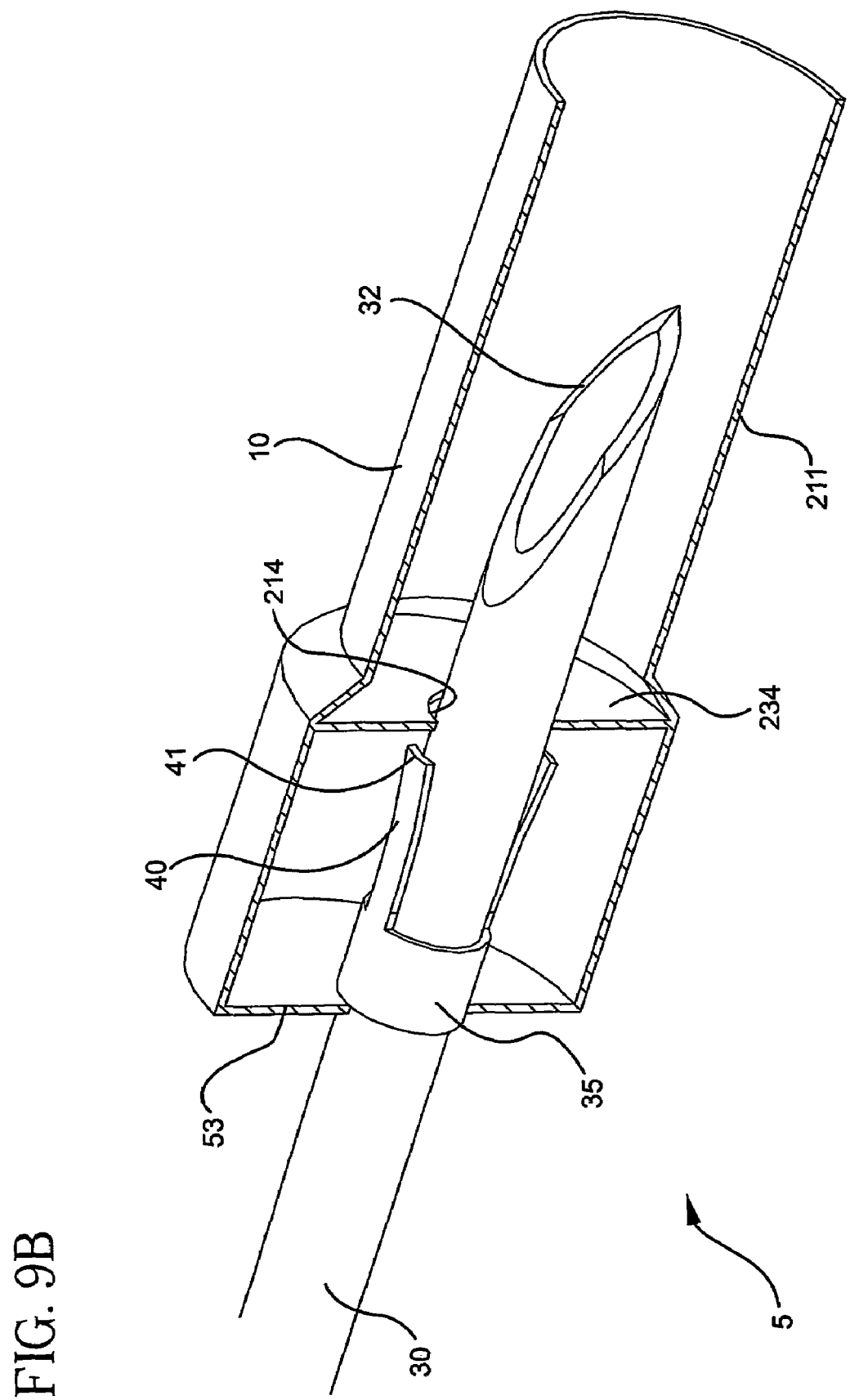
FIG. 9B is a perspective view of the embodiment of the invention shown in FIG. 9A in an actuated condition.
Figure 9C:
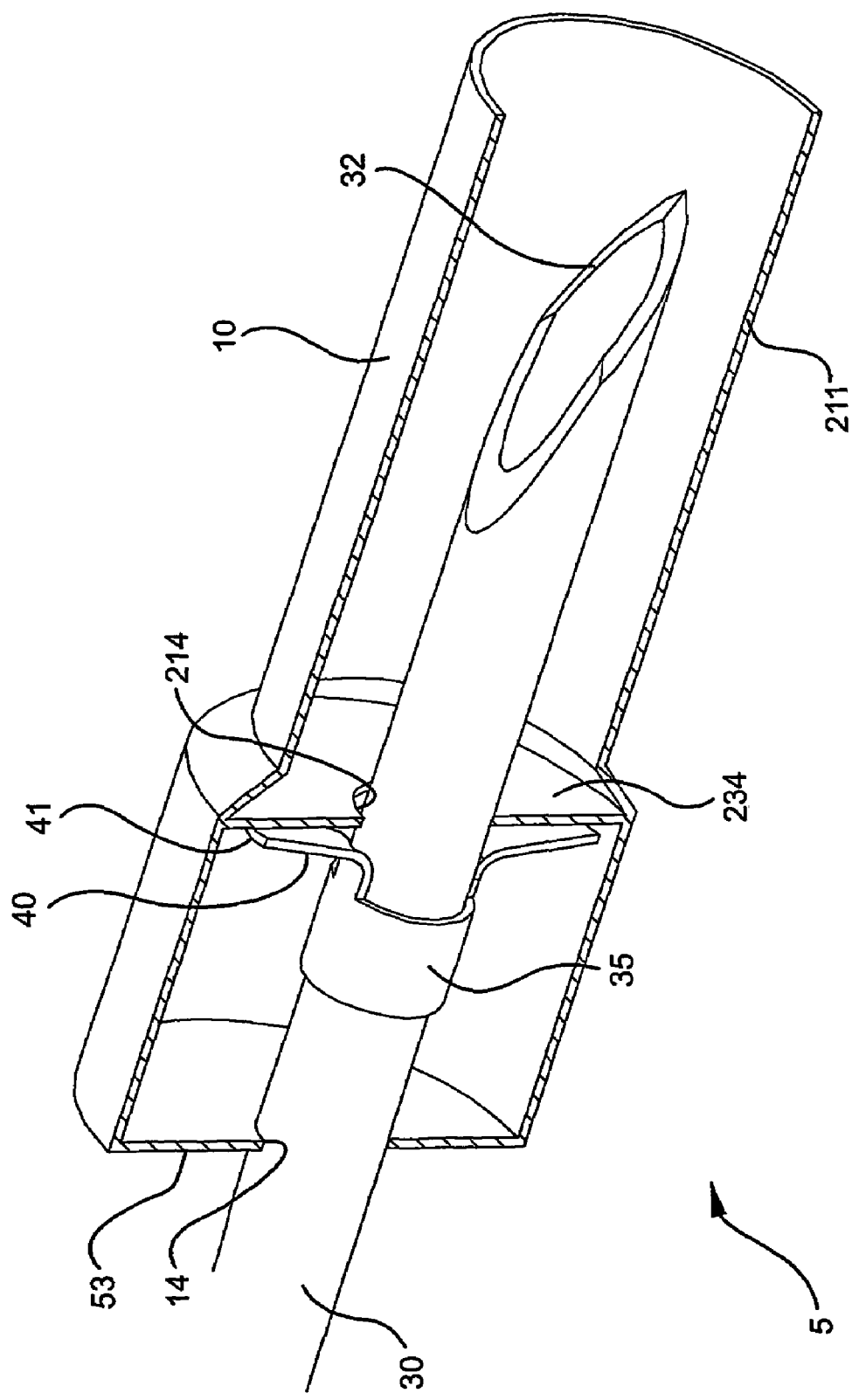
FIG. 9C is a perspective view in partial cross-section of the embodiment of the invention shown in FIG. 9A In an actuated condition and preventing re-emergence of the needle from the needle shield assembly.

Referring now to FIGS. 9A-C, an implementation of the invention is depicted similar to that of FIGS. 8A-B, except the static feature 35 and the elongate member 40 are integrally formed. The needle shield assembly 5 includes a proximal plate 53 having a proximal aperture 14. The shield body 10 is attached to and extends distally from the proximal plate. The distal plate 234 is attached to the shield body at a location distal to the proximal plate 53. The distal plate defines a distal aperture. The shield body 10 extends distally beyond the distal plate such that the shield body will encase the needle tip 32 when In the actuated condition, as discussed below.

A feature 35 is attached to the needle 30. As depicted, the feature Is a ferrule or other band secured about the needle by welding, gluing, friction fitting or the like. The elongate members 40 are integrally formed with the ferrule and extend distally from the ferrule. The elongate members are shaped such that their free ends 141 extend radially away from the exterior of the needle. See, e.g., FIG. 9A. A notch 42 may be included in the needle but it is not deemed necessary for implementation of this aspect of the invention. The distal aperture 214 is sized to permit passage of the ferrule, and to permit passage of the elongate members, once compressed against the side of the needle. The proximal aperture in the proximal plate is sized to prevent passage of the static feature.

In use, the needle shield assembly 5 is slidingly mounted onto the needle 30 such that the tip 32 of the needle is exposed for insertion. After insertion, the needle shield assembly 5 is displaced distally along the needle until the tip 32 of the needle is within the needle shield assembly. (It will be appreciated that, in the context of an over-the-needle catheter assembly 100, the needle is typically withdrawn proximally through the needle shield assembly.) The static feature 35 passes through the distal aperture 214. As the needle 30 is moved further proximally, the distal plate 234 compresses the elongate members 40 against the side of the needle. Once compressed, the elongate members can pass through the distal aperture. The distal plate may be provided with a funnel shape to help direct the passage of the static feature and the compression of the elongate members. As the needle 30 is moved further proximally with respect to the needle shield assembly 5, the static feature 35 contacts the proximal plate 53, preventing further proximal movement of the needle with respect to the needle shield assembly. Should the needle 30 be urged distally with respect to the needle shield assembly 5, the elongate members 40 will engage the distal plate, preventing the needle tip 32 from reemerging from the distal end of the needle shield assembly. See FIG. 9C.

Figure 10A:
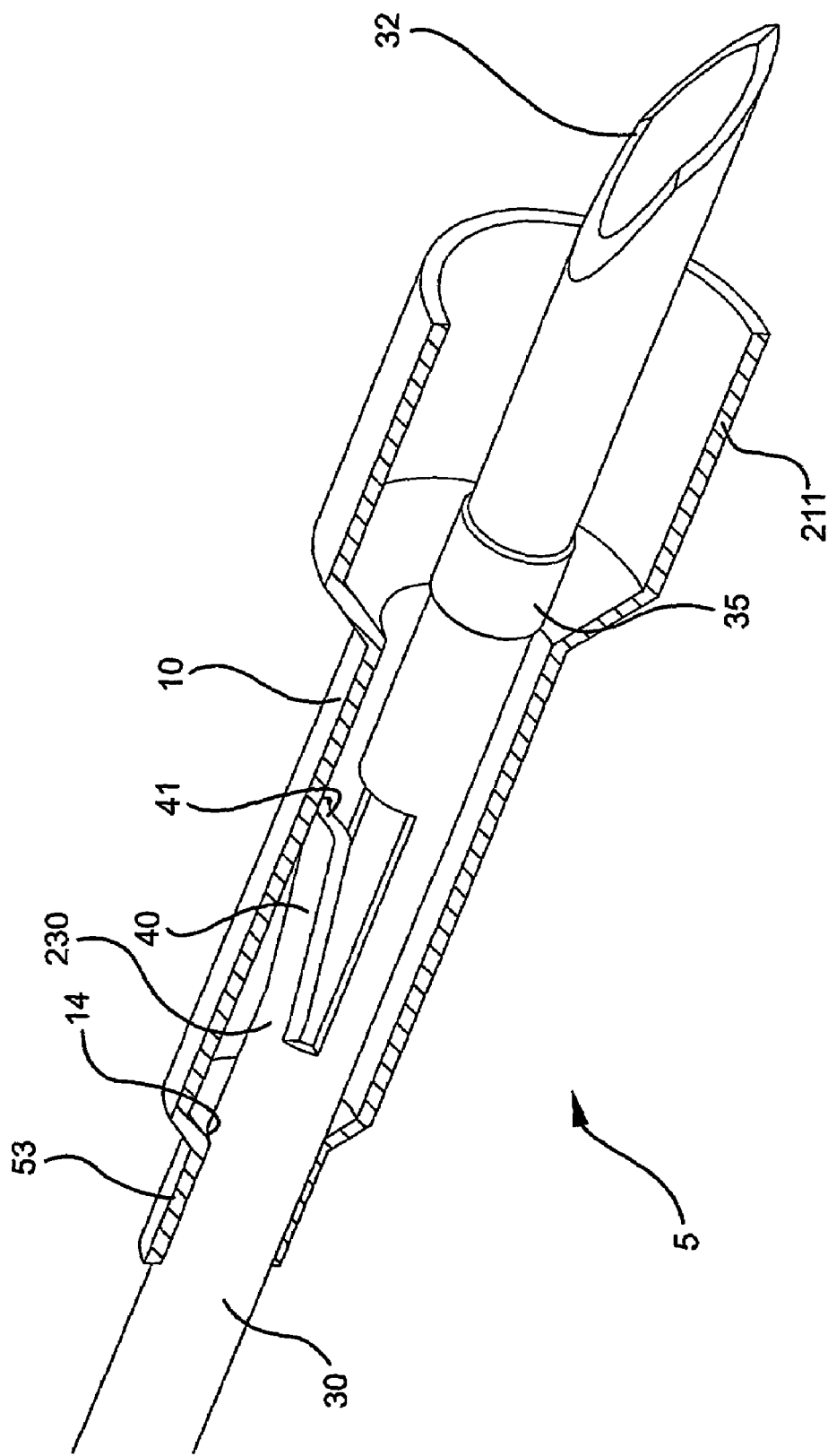
FIG. 10A is a perspective view in partial cross-section of an embodiment of the invention including an elongate member integrally formed with the needle cannula in an unactuated condition.
Figure 10B:
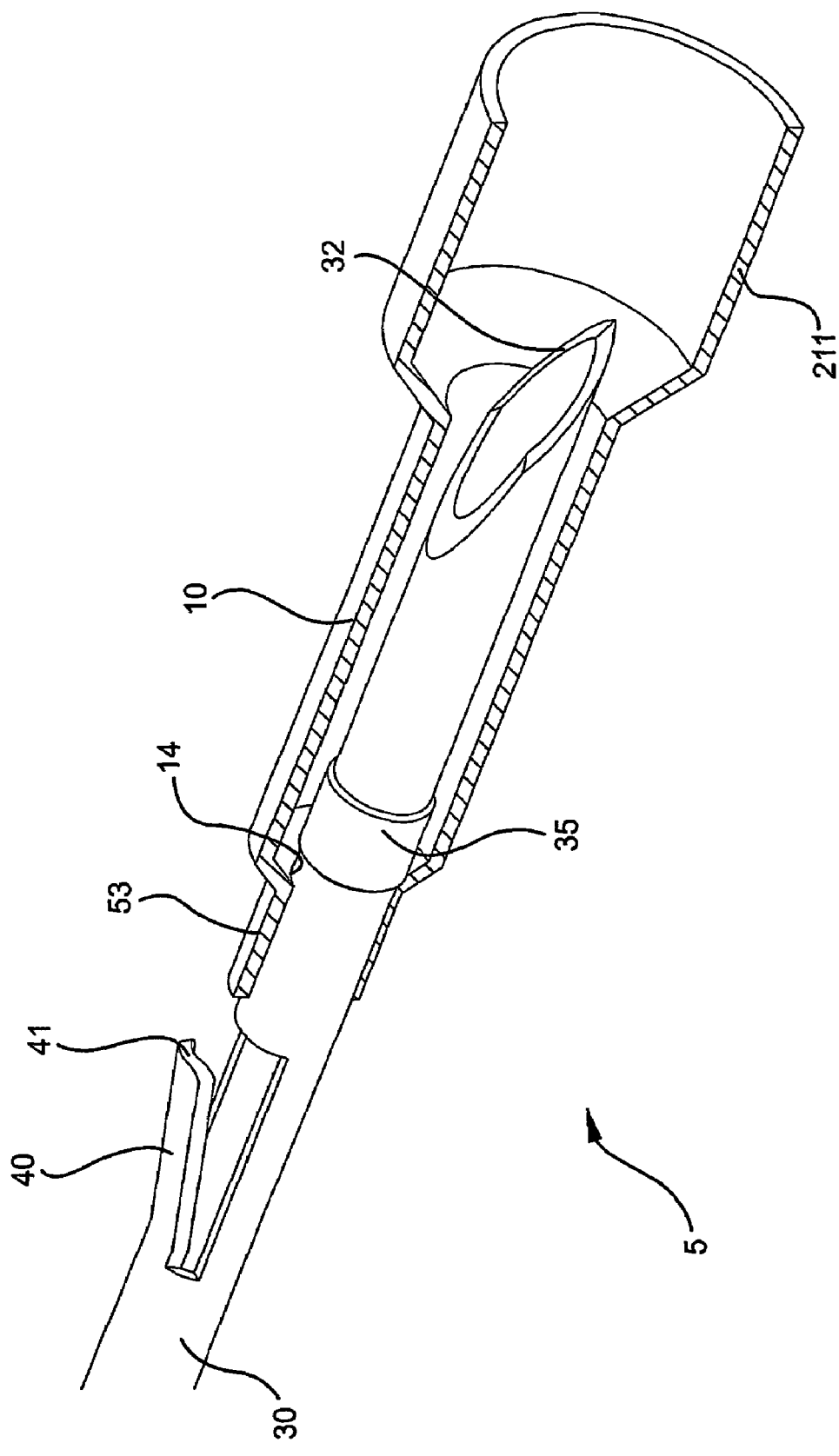
FIG. 10B is a perspective view in partial cross-section of the embodiments of the invention shown in FIG. 10A in an actuated condition.

Referring to FIGS. 10A-B, an implementation of the invention is depicted in which the elastic member, or elongate member 40, is integrally formed with the needle 30. It will be appreciated that this integrated elongate member can be employed with other implementations of the invention discussed herein. The needle shield assembly 5 includes a plate 53, preferably having a cylindrical shape. The shield body 10 is attached to and extends distally from the plate. A portion 42 of the needle Is cut out to form the elongate member as a leaf spring or wire 40 that is biased radially outward from the needle. A static feature 35 is disposed on the needle 30 at a location distal to the elongate member 40. The plate 53 defines an aperture 14 that is shaped and sized to compress the leaf spring 40, allowing the leaf spring to pass through the aperture 14 as the needle is moved proximally with respect to the needle shield assembly. The compression of the leaf spring is aided by the funnel shape of the shield body 10 adjacent to the plate 53. The shield body has a length long enough to ensure that the tip 32 of the needle is encased within the needle shield assembly 5 when the needle shield assembly 5 is moved to an actuated condition at the proximal end of the needle as seen in FIG. 10B.

In use, the needle shield assembly 5 is slidingly mounted onto the needle 30 such that the tip 32 of the needle is exposed for insertion. After insertion, the needle shield assembly 5 is displaced distally along the needle until the tip 32 of the needle is within the needle shield assembly. (It will be appreciated that, in the context of an over-the-needle catheter assembly 100, the needle is typically withdrawn proximally through the needle shield assembly.) As the plate 53 slides over the elongate member or leaf spring 40, it causes the leaf spring to compress into the notch 42 of the needle 30. The formation of the leaf spring results in the notch 42 disposed in the needle 30 being automatically aligned with the leaf spring and thus accommodating the deflection. After the plate 53 passes completely over the leaf spring, the leaf spring returns to its undeformed state, moving radially outward, away from the needle (see FIG. 10B). The needle shield assembly 5 is then prevented from being moved back proximally with respect to the needle 30 to expose the tip of the needle because the plate 53 will engage the leaf spring 40, preventing any further such movement. The aperture 14 of the plate Is sized to prevent passage of the static feature 35. Thus, the needle shield assembly 5 cannot be slipped off the tip 35 of the needle.

Figure 11A:
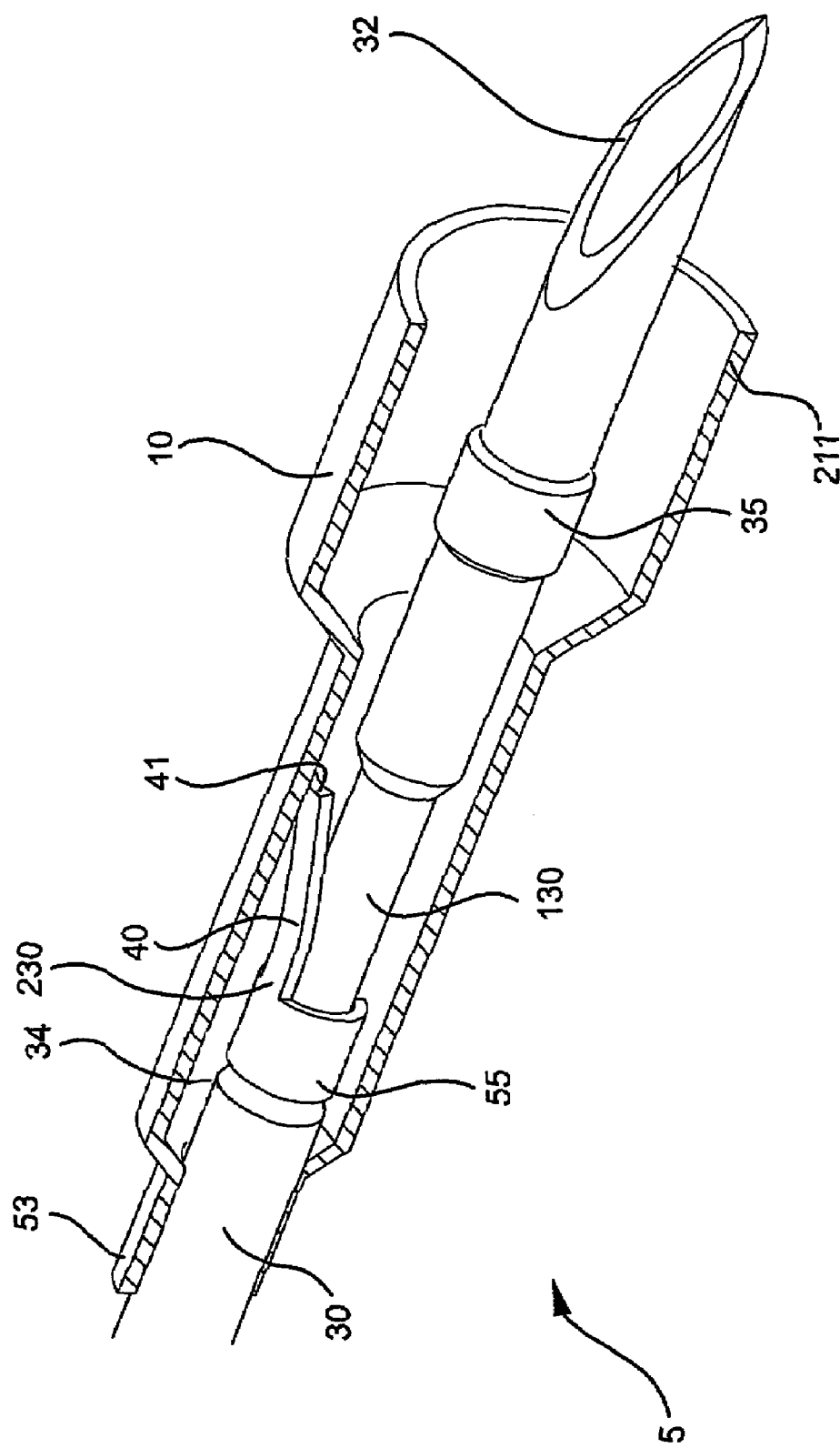
FIG. 11A is a perspective view in partial cross-section of an embodiment of the invention including a ferrule with an integrated elongate member mounted to a reduced diameter portion of the needle shown in an unactuated condition.
Figure 11B:
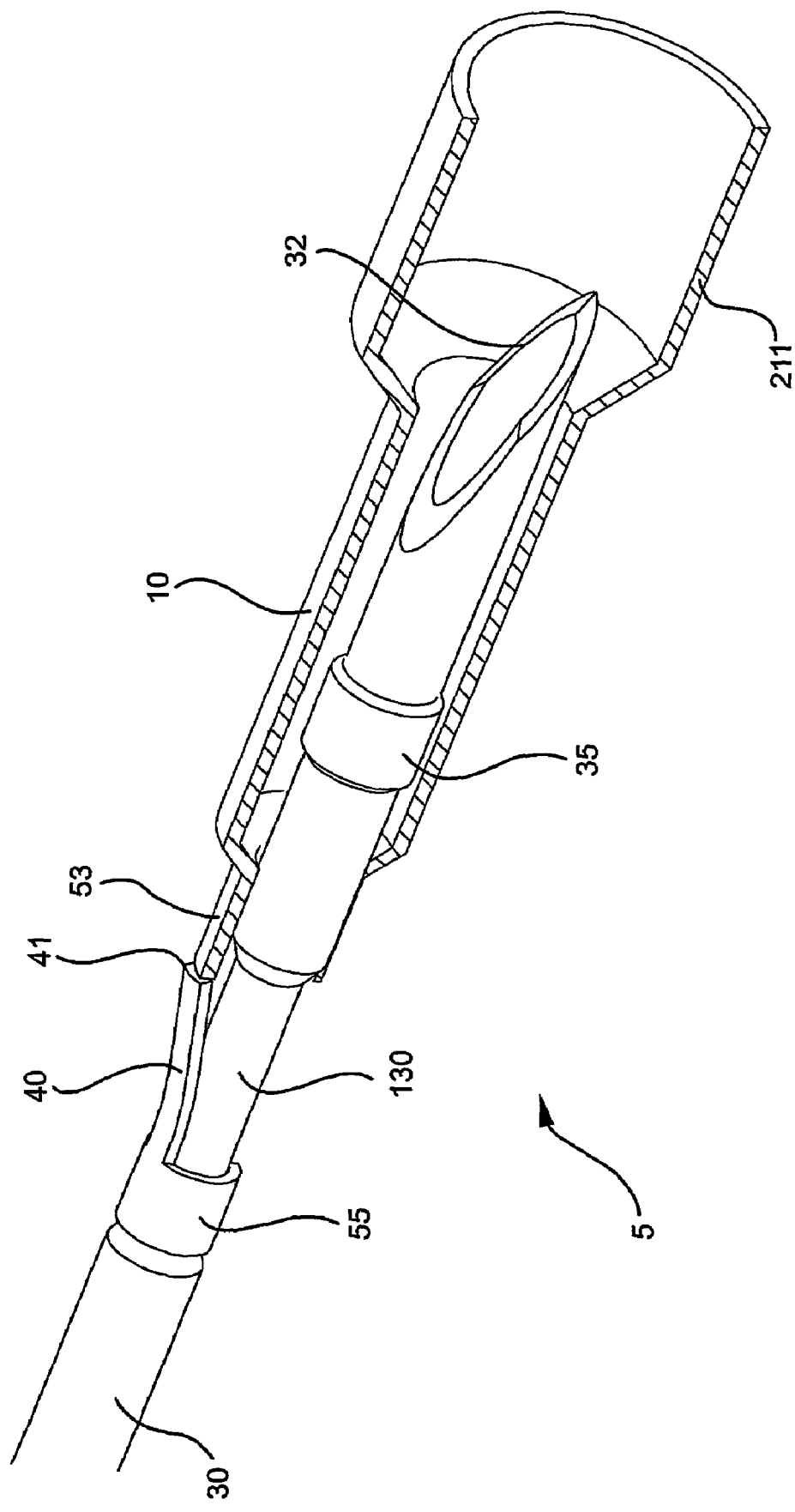
FIG. 11B is a perspective view of the embodiment of the invention shown in FIG. 11A in an actuated condition.

Referring now to FIGS. 11A-B, an implementation similar to that of FIGS. 10A-B is depicted. The needle 30 is provided with a narrow diameter portion 130. A ferrule 55 is attached to the narrow diameter portion 130. Preferably, when attached to the narrow diameter portion, the ferrule 55 has a diameter about the same as or less than the rest of the needle 30. An elongate member 40 is integrally formed with the ferrule and extends in a distal direction. The plate 53 includes an aperture 14 sized to permit passage of the needle and the ferrule. During actuation, the plate 53 will cause the elongate member 40 to flex onto the narrow diameter portion 130, permitting the elongate member to pass through the aperture 14 as well. Once the elongate member 40 passes beyond the plate 53 completely, it flexes radially out of the narrow diameter portion 130 of the needle. Consequently, free end 41 of the elongate member 40 cannot pass back through the aperture and the needle shield assembly 5 is trapped on the needle, preventing re-exposure of the needle tip 32.

Figure 12A:
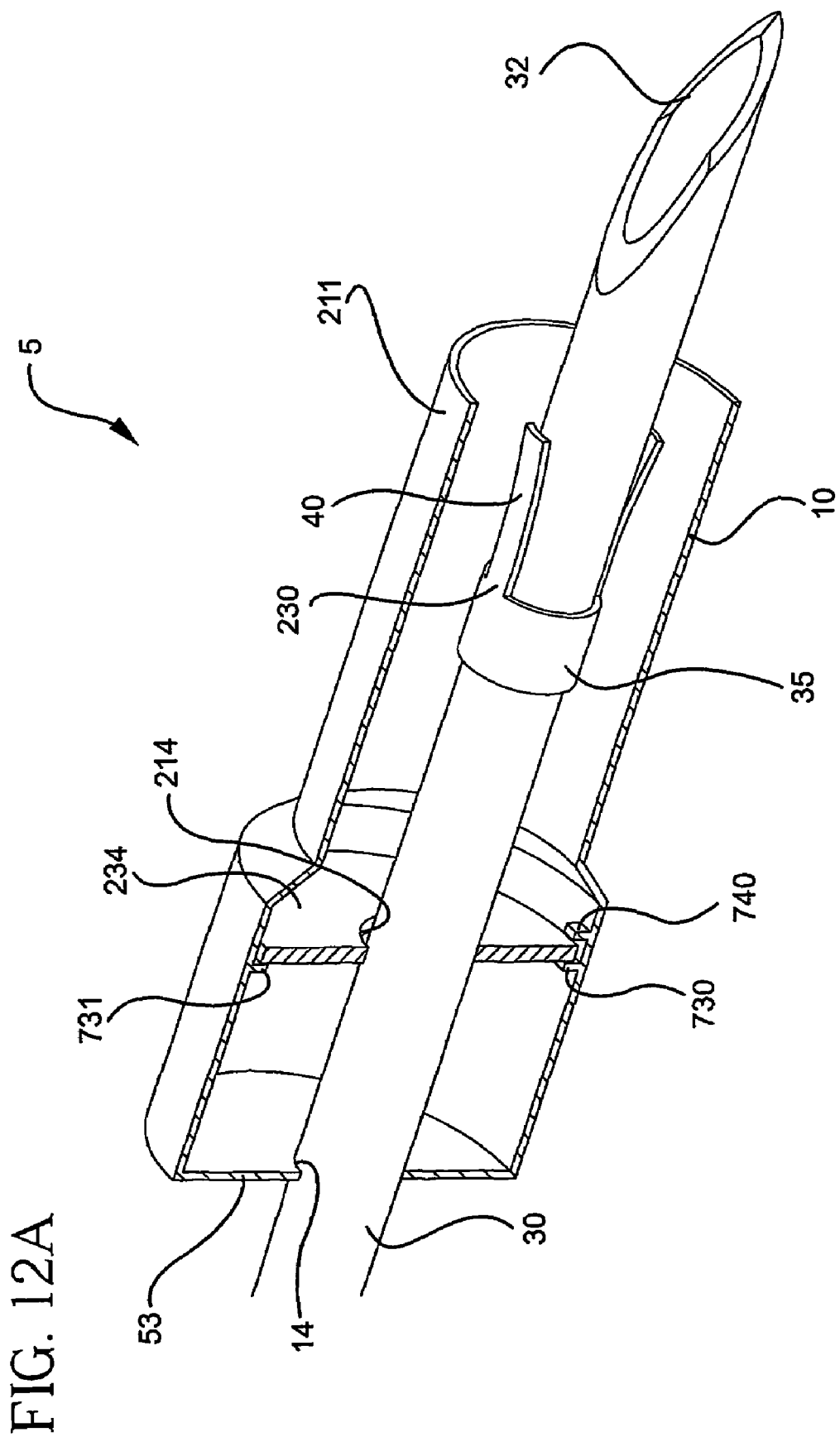
FIG. 12A is a perspective view in partial cross-section of an embodiment of the invention including a distal plate adapted to tilt and bind the exterior of the needle shown in an unactuated condition.
Figure 12B:
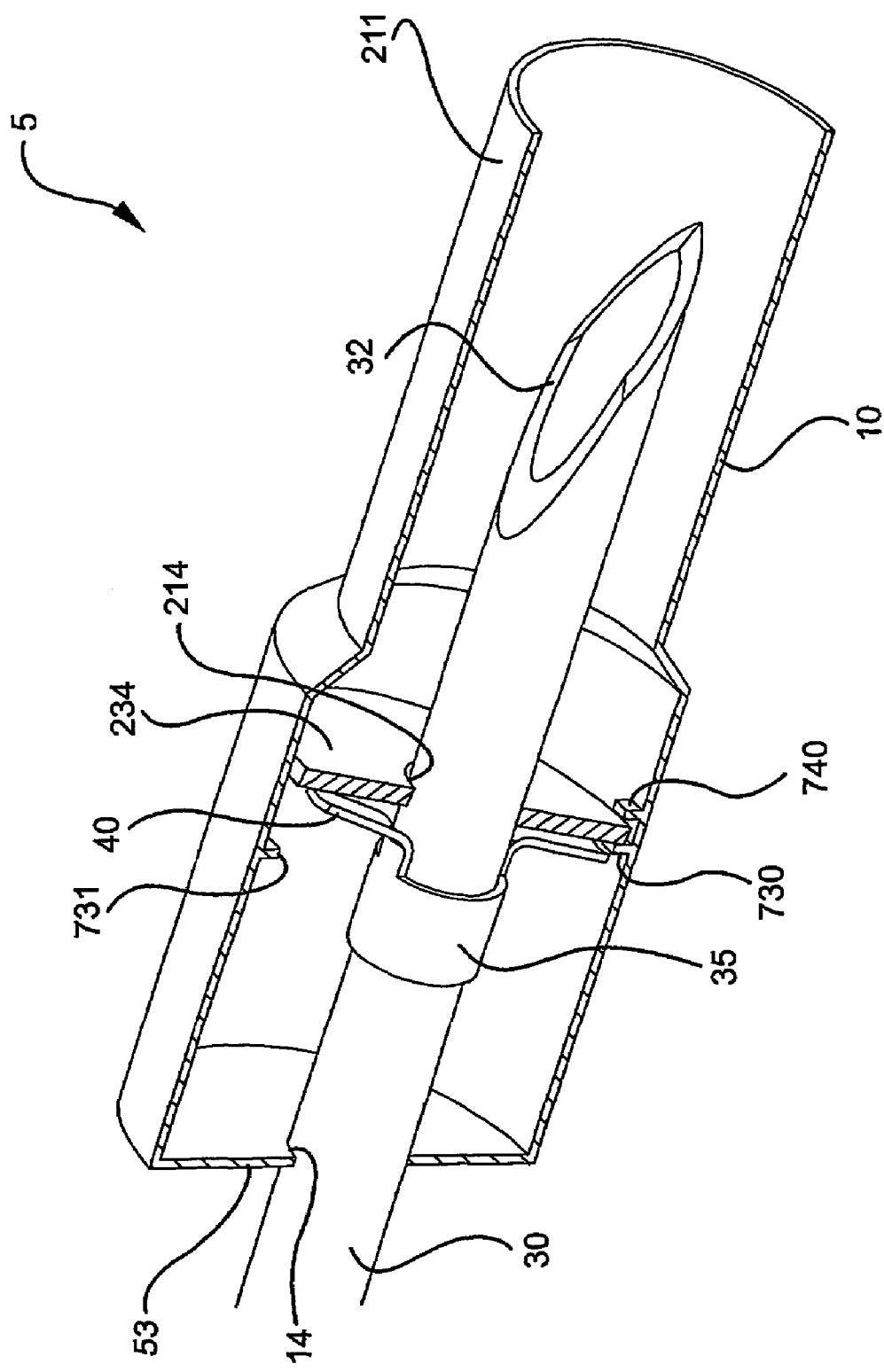
FIG. 12B is a perspective view in partial cross-section of the embodiment of FIG. 12A shown in an actuated condition.

Referring to FIGS. 12A-B, an Implementation of the invention is depicted which is similar to that of FIGS. 9A-C. The distal plate 234 in this instance is a tilting or canting plate engaged at one end between a proximal ledge 730 and a distal ledge 740. An additional proximal ledge 731 is provided to prevent tilting of the distal plate during withdrawal of the needle 30 tip within the needle shield assembly 5.

In use, the needle shield assembly 5 is slidingly mounted onto the needle 30 such that the tip 32 of the needle is exposed for insertion. After insertion, the needle shield assembly 5 is displaced distally along the needle until the tip 32 of the needle is within the needle shield assembly. (It will be appreciated that, in the context of an over-the-needle catheter assembly 100, the needle is typically withdrawn proximally through the needle shield assembly.) The static feature 34 passes through the distal aperture 214. As the needle 30 is moved further proximally, the distal plate 234 compresses the elongate members 40 against the side of the needle. The distal plate is prevented from tilting because of the ledges 730, 740 and 731. Once compressed, the elongate members 40 can pass through the distal aperture 214. The distal plate 234 may be provided with a funnel shape to help direct the passage of the static feature and the compression of the elongate members. As the needle 30 is moved further proximally with respect to the needle shield assembly 5, the static feature 35 contacts the proximal plate 53, preventing further proximal movement of the needle with respect to the needle shield assembly. Should the needle 30 be urged distally with respect to the needle shield assembly 5, the elongate members will engage the distal plate 234, causing it to tilt. The distal plate is prevented from moving distally with the needle because of the lower ledges 730, 740. Once tilted, the distal plate 234 will bind onto the exterior of the needle, preventing further distal movement of the needle with respect to the distal plate.

The implementations of the invention depicted above include a plate 53 and a shield body 10 integrally formed with and extending distally from the plate. It will be appreciated that the plate and the shield body can be distinct members, operatively engaged such that the restriction of movement of the plate 53 exacted by the static feature 35 and the elongate members 40 results in the containment of the needle shield assembly 5 over-the-needle tip 32. The plate 53 itself may have other shapes so long as it cooperates with the elongate members 40 to prevent the return proximal movement of the needle shield assembly 5. For example, the plate may have a conical shape, narrowing in the proximal direction. This shape may help guide the elongate members 40 into the notch 42. The elongate member is depicted aligned with the notch. The elongate members could also be attached to the needle at some other point, not in alignment with the notch. In such a case, the aperture 14 in the plate 53 would need to accommodate the elongate member and needle as the plate moved distally over the elongate members, but still be small enough to prevent passage of the static feature. Further, the aperture must be sized small enough such that it does not permit the free end 41 of the elongate members, in its extended position, to pass.

As shown, either one or two elongate members 40 are used to engage the plate 53. It will be appreciated that other numbers of elongate members may be employed, depending upon the specific application, and still practice aspects of the invention. Further, it is apparent that the elongate member 40 is used to restrict the movement of the shield 5 with respect to the needle 30. The shield should be of a length adequate to ensure that, as so restricted, the tip 32 of the needle cannot emerge from out of the shield. In certain implementations, this may be achieved by ensuring that the portion of the shield distal to the plate is longer than the distance between the connection point 230 and the needle tip.

As depicted above, the static feature 35 is used to prevent the needle shield assembly 5 from sliding off the tip 32 of the needle 30. It will be appreciated that other mechanisms, such as a tether or canting plate may be used to prevent the needle shield assembly from sliding off the needle tip and still practice aspects of the invention.

It will be appreciated that components of the foregoing implementations of the inventions may be combined and still practice aspects the invention. The foregoing description is not deemed to be a limitation on the invention, which is defined by the following claims.

We claim:

1. An introducer needle and catheter assembly comprising:
    a needle cannula having a body and a tip, wherein the tip is disposed at a distal end of the cannula, and the cannula defining a notch disposed in the needle cannula;
    a needle shield assembly disposed about the needle cannula; and
    an elongate member, fixedly attached to the needle cannula at a connection point and extending through the notch in the cannula;
    wherein the elongate member is displaceable from an unbiased condition remote from the needle cannula to a biased condition near the needle cannula, and cooperates with the needle shield assembly so that the needle shield assembly may not be displaced proximate of the elongate member after distally passing the elongate member such that when the tip is positioned within the needle shield re-emergence of the tip from the shield is prevented.

2. The introducer needle and catheter assembly of claim 1 wherein the elongate member is integrally formed with the needle cannula.

3. The introducer needle and catheter assembly of claim 1 wherein the elongate member is a leaf spring.

4. The introducer needle and catheter assembly of claim 1 wherein the elongate member is a wire.

5. The introducer needle and catheter assembly of claim 1 wherein the elongate member is a leaf spring aligned with the notch, wherein, in the biased condition, the leaf spring is disposed within the notch.

6. A needle shield assembly comprising:
    a needle shield;
    a needle having a tip and positioned such that it passes through the needle shield;
    a ferrule defined on the needle which cooperates with the needle shield to prevent withdrawal of the needle from the needle shield beyond a predetermined point;
    an elongate member fixedly attached to the needle such that when the needle is withdrawn a predetermined distance with respect to the needle shield and the needle tip is positioned within the needle shield, the elongate member extends to prevent re-emergence of the needle tip from the needle shield wherein the needle further comprises a notch and wherein the elongate member is disposed within the notch.

7. A needle shield assembly as defined in claim 6 wherein the elongate member is a leaf spring.

8. A needle shield assembly as defined in claim 6 wherein the elongate member is a wire.

9. A needle shield assembly as defined in claim 6 wherein the elongate feature is compressed toward the needle by a structure of the needle shield upon withdrawal of the needle through the needle shield until the needle reaches a predetermined point at which point the elongate feature extends outwardly from the needle.

10. A needle shield assembly as defined in claim 9 wherein the structure of the needle shield is a plate.

11. A needle shield assembly comprising:
    a needle shield;
    a needle having a tip and positioned such that it passes through the needle shield;
    a ferrule defined on the needle which cooperates with the needle shield to prevent withdrawal of the needle from the needle shield beyond a predetermined point;
    an elongate member fixedly attached to the needle such that when the needle is withdrawn a predetermined distance with respect to the needle shield and the needle tip is positioned within the needle shield, the elongate member extends to prevent re-emergence of the needle tip from the needle shield;
    wherein the needle further comprises a notch and wherein the elongate member is disposed within the notch.

* * * * *